US011718825B2

(12) United States Patent
Mitalipov et al.

(10) Patent No.: US 11,718,825 B2
(45) Date of Patent: Aug. 8, 2023

(54) GENERATION OF HUMAN OOCYTES

(71) Applicant: Oregon Health & Science University, Portland, OR (US)

(72) Inventors: Shoukhrat Mitalipov, Beaverton, OR (US); Nuria Marti-Gutierrez, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 1126 days.

(21) Appl. No.: 16/347,949

(22) PCT Filed: Nov. 8, 2017

(86) PCT No.: PCT/US2017/060720
§ 371 (c)(1),
(2) Date: May 7, 2019

(87) PCT Pub. No.: WO2018/089553
PCT Pub. Date: May 17, 2018

(65) Prior Publication Data
US 2019/0292519 A1 Sep. 26, 2019

Related U.S. Application Data

(60) Provisional application No. 62/427,546, filed on Nov. 29, 2016, provisional application No. 62/419,638, filed on Nov. 9, 2016.

(51) Int. Cl.
| | | |
|---|---|---|
| *C12N 5/075* | (2010.01) | |
| *A61B 17/435* | (2006.01) | |
| *C12N 5/073* | (2010.01) | |
| *C12N 5/16* | (2006.01) | |
| *A61K 35/00* | (2006.01) | |

(52) U.S. Cl.
CPC .......... *C12N 5/0609* (2013.01); *A61B 17/435* (2013.01); *C12N 5/0604* (2013.01); *C12N 5/16* (2013.01); *A61K 35/00* (2013.01); *C12N 2517/04* (2013.01); *C12N 2517/10* (2013.01)

(58) Field of Classification Search
CPC .............. C12N 5/0609; C12N 5/0604; C12N 2517/04; C12N 2517/10
USPC ............................................ 600/34; 800/25
See application file for complete search history.

(56) References Cited

U.S. PATENT DOCUMENTS

| | | |
|---|---|---|
| 6,143,564 A | 11/2000 | Wakayama et al. |
| 2014/0308257 A1 | 10/2014 | Egli |
| 2014/0335619 A1 | 11/2014 | Mitalipov et al. |

FOREIGN PATENT DOCUMENTS

| | | |
|---|---|---|
| WO | WO 2008/144580 | 11/2008 |
| WO | WO 2009/015036 | 1/2009 |
| WO | WO 2010/124123 | 10/2010 |
| WO | WO 2018/195418 | 10/2018 |

OTHER PUBLICATIONS

Gruber, J Turkish-German Gynecol Assoc 2011; 12: 110-7.*
International Search Report and Written Opinion mailed in International Application No. PCT/US2017/060720, dated Mar. 26, 2018, 9 pages.
Kang et al., "Mitochondrial Replacement in Human Oocytes Carrying Pathogenic Mitochondrial DNA Mutations," *Nature*, vol. 540, No. 7632, pp. 270-275 (Dec. 8, 2016).
Li et al., "Physiology and pathophysiology of mitochondrial DNA," *Advances in Experimental Medicine and Biology*, vol. 942, pp. 1-17 (Jan. 8, 2016).
Ma et al., "Functional Human Oocytes Generated by Transfer of Polar Body Genomes," *Cell Stem Cell*, vol. 20, Iss. 1, pp. 112-119 (Jan. 5, 2007).
Tsai et al., "The relationship between mitochondrial DNA haplotype and the reproductive capacity of domestic pics (sus scrofa domesticus)," *BMC Genetics*, vol. 17, No. 67, pp. 1-17 (May 18, 2016).
Wang et al., "Polar body genome transfer for preventing the transmission of inherited mitochondrial diseases," *Cell* 157: 1591-1604 (Jun. 19, 2014).
Hurle, "Somatic Cells," printed from the U.S. web at: https://www.genome.gov/genetics-glossary/Somatic-Cells (Dec. 27, 2022).
Santos et al., "Usefulness of bovine and porcine IVM/IVF models for reproductive toxicology," *Reproductive Biology and Endocrinology* 12:117, 12 pages (Nov. 26, 2014).
Schmerler and Wessel, "Polar Bodies—more a lack of understanding than a lack of Respect," *Mol Reprod Dev.* 78(1): 3-8 (Jan. 1, 2011).

\* cited by examiner

*Primary Examiner* — Valarie E Bertoglio
(74) *Attorney, Agent, or Firm* — Klarquist Sparkman, LLP

(57) ABSTRACT

Methods are provided of generating functional human oocytes following nuclear transfer of first polar body (PB1) genomes from metaphase II (MII) oocytes into enucleated donor MII cytoplasm (PBNT) and using mitochondrial replacement techniques to circumvent mother-to-child mtDNA disease transmission.

6 Claims, 33 Drawing Sheets

Family 1  Family 2

Family 3

Family 5

Correlation in mutation levels between oocytes and blood of carriers or children

Figure 10A

Information on families with mitochondrial disease

| Mitochondria disease | Family | Affected member | Age (yr) | Clinical manifestation | Mother's age (yr) | mtDNA mutation | Gene |
|---|---|---|---|---|---|---|---|
| Leigh syndrome | F1 | Daughter | 2 | Seizures, metabolic acidosis, developmental delay, difficulty to thrive, abnormal basal ganglia and enlargement heart ventricle | 22 | T8993G | ATP6 (non-syn) |
| | F2 | Son | 2.5 | Seizures, chronic acidosis, developmental delay, difficulty to thrive and encephalopathy | 23 | T8993G | ATP6 (non-syn) |
| | F3 | Son | 12 | Seizures, failure to thrive, difficulty in breathing, enlarged heart ventricle, kidney failure and optic nerve atrophy | 36 | G13513A | ND5 (non-syn) |
| | F4 | Daughter | 1 | Seizures, difficulty to thrive, lactic acidosis, neuro-motor impairment and history of congenital brain abnormality | 28 | No | n/a |
| MELAS syndrome | F5 | Maternal sister | 23 | Mitochondrial encephalomyopathy, lactic acidosis and stroke-like episodes | 32 | A3243G | tRNA (Leucine) |

Figure 10B

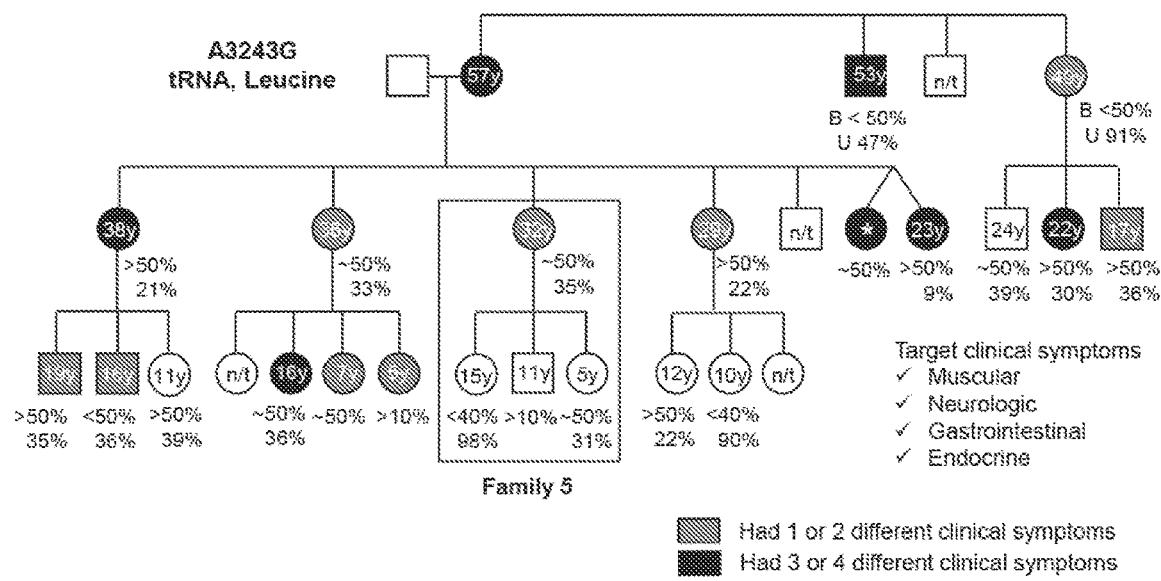

Responses to controlled ovarian stimulation in women carrying pathogenic mtDNA mutations

| Oocyte donor | Family | Age (yr) | Duration of birth control (yr) | BMI (kg/m²) | AMH (ng/ml) | AFC (N) | Peak E2 (pg/ml) | Duration of Stimulation (days) | Retrieved Oocytes (N) | Mature MII oocytes (N) |
|---|---|---|---|---|---|---|---|---|---|---|
| cED1 | F1 | 22 | 2 | 22.1 | 0.2 | 9 | 280 | 11 | 3 | 2 |
| cED2 | F2 | 23 | none | 34.1 | 3.3 | 10 | 797 | 11 | 5 (premature luteinization) | n/a |
| cED3 | F3 | 36 | 12 | 23.5 | 0.5 | 8 | 1848 | 12 | 4 | 4 |
| cED4 | F5 | 32 | none | 33.1 | 0.4 | 14 | 2156 | 12 | 11 | 9 |

Figure 12A

Donor oocyte mtDNA haplotypes and SNP differences in ST embryos

| Cyto\Karyo | Egg donor | hED1 (21-yr) | hED2 (29-yr) | hED3 (23-yr) | hED4 (25-yr) | hED5 (25-yr) | hED6 (28-yr) | hED7 (24-yr) | hED8 (34-yr) | hED9 (32-yr) | hED10 (27-yr) | hED11 (29-yr) |
|---|---|---|---|---|---|---|---|---|---|---|---|---|
| Egg donor | mtDNA haplotype | L2c | D4a | A2g | B2k | U5a | V3 | T2 | H1b | H2a | H6a | H56 |
| hED1 (21-yr) | L2c | | | | | | | | | 57 | | |
| hED2 (29-yr) | D4a | | | 49 | | | | | | | | |
| hED3 (23-yr) | A2g | | 49 | | | | | | | | | |
| hED5 (25-yr) | U5a | | | | | | 33 | | 33 | | | |
| hED6 (28-yr) | V3 | | | | 33 | | | | | | | |
| hED8 (34-yr) | H1b | | | | 33 | | | | | | | |
| hED9 (32-yr) | H2a | 57 | | | | | | | | | | 6 |
| hED11 (29-yr) | H56 | | | | | | | | | 6 | | |
| cED1 (22-yr) | H1b | | | | | | | | | | 20 | |
| cED3 (36-yr) | T2b | | | | | | | 22 | | | | |
| cED4 (32-yr) | H49 | | | | 32 | | | | | | | |

Figure 12B

Fertilization abnormalities in ST zygotes

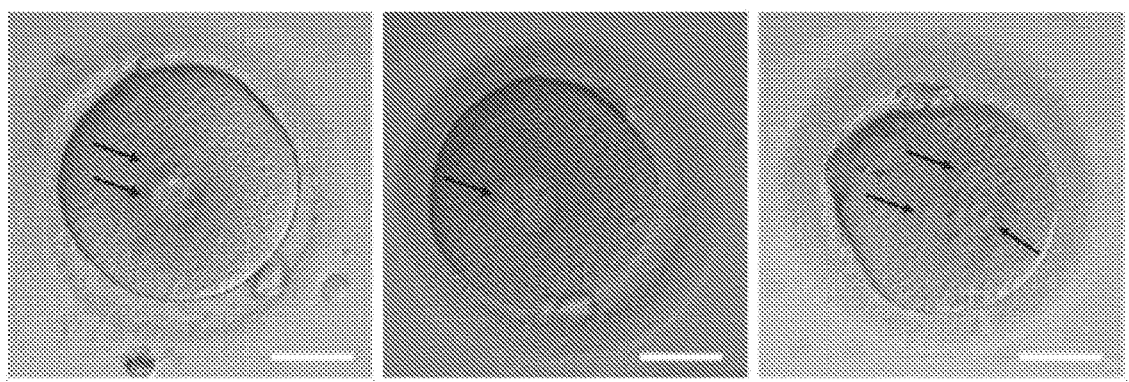

Normal zygote with 2 pronuclei Abnormal zygote with one pronuclus Abnormal zygote with 3 pronuclei

Figure 12C

Fertilization abnormalities in ST zygotes and embryos

| Treatment | Total fertilized zygotes (N) | Total abnormal fertilized zygotes (%) | Abnormal No. of pronuclei | | | Blastocysts | Karyotypes |
| --- | --- | --- | --- | --- | --- | --- | --- |
| | | | One | Three (%) | Abnormal divided | | |
| Intact control | 17 | 1 (6) | 1 | 0 | 0 | 0 | |
| Control ST | 32 | 2 (6) | 1 | 0 | 0 | | |
| | | | | 1 (3) | | 1 | 69,XXY |
| Carrier ST | 12 | 4 (33) | 1 | 2 (17) | 1 | 0 | |

Figure 12D

Fertilization and embryo development of frozen ST oocytes

| Treatment | MII oocytes (N) | Survived after ST (%) | Total fertilization (%) | Normal fertilization (%) | Abnormal N. pronuclei | | Normal morale (%) | Normal blastocysts (%) |
| --- | --- | --- | --- | --- | --- | --- | --- | --- |
| | | | | | One | Three (%) | | |
| Vitrified cytoplasts/ Fresh spindles | 6 | 6 (100) | 6 (100) | 4 (67) | 1 | 1 (17) | 4 (100) | 1 (25) |
| Vitrified spindles/ Fresh cytoplasts | 6 | 6 (100) | 3 (50) | 2 (67) | 0 | 1 (33) | 2 (100) | 1 (50) |

Figure 12E

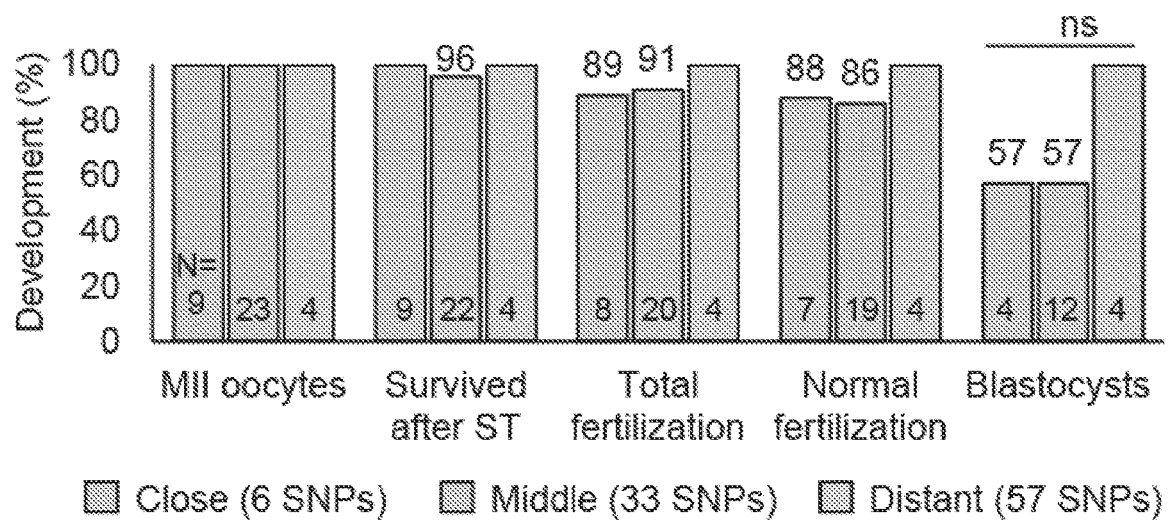

Figure 13B

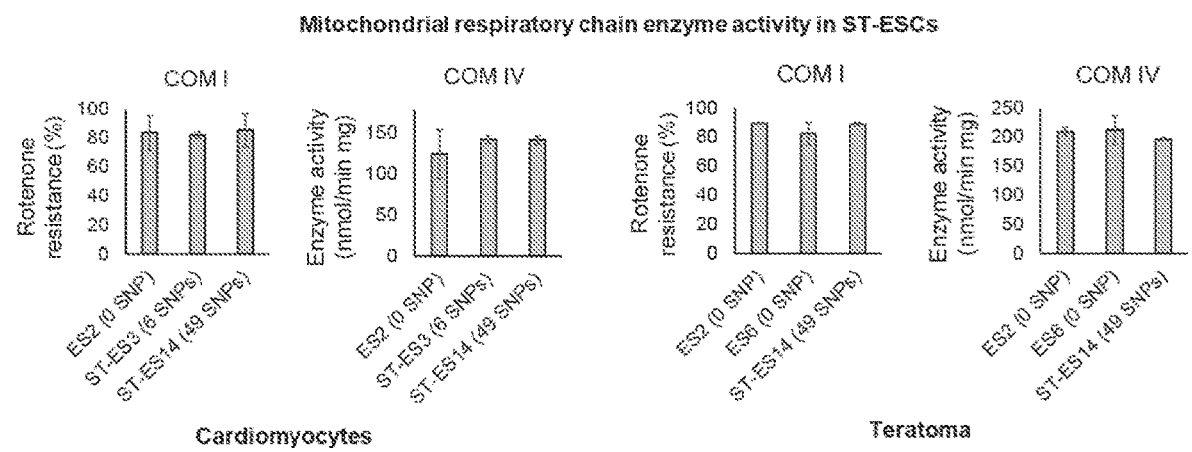

Figure 14A

*In vivo* and *in vitro* differentiation of MRT-ESCs

| No. | Cell line | Maternal mtDNA haplotype | Donor mtDNA haplotype(s) | SNP difference | Teratoma | NPCs | Cardiomyocytes |
|---|---|---|---|---|---|---|---|
| 1 | ES1 | H1b control | | 0 | nt | yes | yes |
| 2 | ES2 | D4a control | | 0 | yes | yes | yes |
| 3 | ES3 | H56 control | | 0 | nt | yes | yes |
| 4 | ES6 | A2g control | | 0 | yes | yes | yes |
| 5 | ST-ES3 | H2a | H56 | 6 | nt | yes | yes |
| 6 | ST-ES6 | H1b | U5a | 33 | nt | yes | yes |
| 7 | ST-ES7 | U5a | H1b/ U5a (reversed) | 33 | nt | yes | yes |
| 8 | ST-ES14 | D4a | A2g | 49 | yes | yes | yes |
| 9 | ST3243-ES1 | H49 | B2k/ H49 (reversed) | 31 | yes | yes | yes |
| 10 | ST3243-ES2 | H49 | B2k | 31 | yes | yes | yes |
| 11 | NT-ES8 | X2c | D4a/ X2c (reversed) | 39 | yes | yes | yes |

Summary of array CGH in intact and ST blastocysts

| Treatment | # | Age of nuclear donor (yr) | Egg donor ID | aCGH Results | Sex |
|---|---|---|---|---|---|
| Intact control | 1 | 34 | hED8 | Abnormal: -21 | Male |
| | 2 | 29 | hED11 | Normal | Male |
| | 3 | 25 | hED4 | Normal | Female |
| | 4 | 25 | hED4 | Normal | Male |
| Control ST | 1 | 34 | hED8 | Abnormal: +7, +15 | Male |
| | 2 | 32 | hED9 | Normal | Male |
| | 3 | 32 | hED9 | Normal | Female |
| | 4 | 32 | hED9 | Normal | Male |
| | 5 | 29 | hED11 | Abnormal: +12 | Male |
| | 6 | 21 | hED1 | Normal | Male |
| Carrier ST | 1 | 36 | cED3 | Abnormal: +9 | Male |
| | 2 | 32 | cED4 | Normal | Female |

Figure 15B

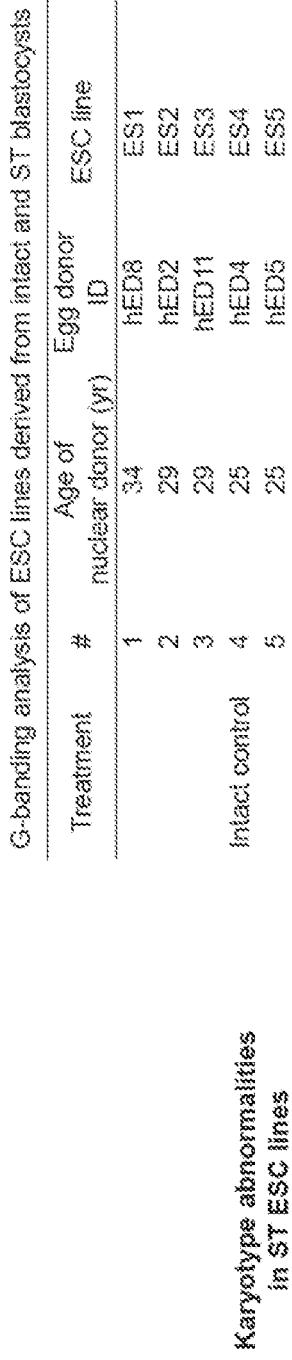

G-banding analysis of ESC lines derived from intact and ST blastocysts

| Treatment | # | Age of nuclear donor (yr) | Egg donor ID | ESC line | Karyotype |
|---|---|---|---|---|---|
| Intact control | 1 | 34 | hED8 | ES1 | 46,XX |
|  | 2 | 29 | hED2 | ES2 | 46,XX |
|  | 3 | 29 | hED11 | ES3 | 46,XY |
|  | 4 | 25 | hED4 | ES4 | 46,XY |
|  | 5 | 25 | hED5 | ES5 | 46,XX |
|  | 6 | 23 | hED3 | ES6 | 46,XX |
|  | 7 | 23 | hED3 | ES7 | 45,XY,-21 |
| Control ST | 1 | 34 | hED8 | ST-ES5 | Mosaicism 47,XX +10 [12]/46,XX [8] |
|  | 2 | 34 | hED8 | ST-ES6 | 46,XX |
|  | 3 | 32 | hED9 | ST-ES3 | 46,XX |
|  | 4 | 29 | hED2 | ST-ES14 | 46,XY |
|  | 5 | 28 | hED6 | ST-ES10 | 45,X |
|  | 6 | 25 | hED5 | ST-ES7 | 46,XY |
|  | 7 | 25 | hED5 | ST-ES8 | 92,XXXX |
|  | 8 | 25 | hED5 | ST-ES9 | 46,XY |
| Carrier ST | 1 | 36 | cED3 | 13513 ST-ES | 47,XY,+9 |
|  | 2 | 32 | cED4 | 3243 ST-ES1 | 46,XX |
|  | 3 | 32 | cED4 | 3243 ST-ES2 | 46,XY |

Figure 17

| Treatment | # | ESC line ID | CNVs | Chromosome Location | CNV chromosome | Interpretation |
|---|---|---|---|---|---|---|
| Intact control | 1 | ES1 | Deletion (neutral) | 15q11.2 | male | 699 kb region of chromosome 15 (15q11.2) shows low level mosaicism (approximately 10%-20%) for homozygosity of uncertain clinical significance. |
| | 2 | ES5 | Deletion (neutral) | 15q11.2 | male | 1.1 Mb region of chromosome 15 (15q11.2) shows mosaicism for homozygosity of uncertain clinical significance. |
| | | | Deletion (neutral) | Xp22.33-q28 | male | Less than 10% of cells of the entire chromosome X (Xp22.33-Xq28) of uncertain clinical significance. |
| Control ST | 1 | ST-ES5 | Duplication | 10p15.3-q26.3 | male | Mosaic trisomy 10. |
| | | | Deletion (neutral) | 15q11.2 | male | 549 kb region of chromosome 15 (15q11.2) shows mosaicism for homozygosity of uncertain clinical significance. |
| | | | Deletion | Xp22.33-q28 | male | Monosomy X (Xp22.33-Xq28) of uncertain clinical significance. |
| | 2 | ST-ES6 | None | n/a | | n/a |
| | 3 | ST-ES7 | None | n/a | | n/a |
| | 4 | ST-ES9 | None | n/a | | n/a |
| Carrier ST | 1 | 3243ST-ES1 | None | n/a | | n/a |
| | 2 | 3243ST-ES2 | Deletion (neutral) | 15q11.2 | male | 791 kb region of chromosome 15 (15q11.2) shows mosaicism for homozygosity of uncertain clinical significance. |

Figure 18

|  | Family 1 | Family 2 | Family 3 | Family 4 | Family 5 |  |  |  |
|---|---|---|---|---|---|---|---|---|
| Mitochondrial disease | LS | LS | LS | LS | MELAS |  |  |  |
| Pathogenic mtDNA mutation | T8993G | T8993G | G13513A | No | A3243G |  |  |  |
| Age of carrier (yr) | 22 | 23 | 36 | 28 | 32 |  |  |  |
| COS | Yes | Yes | Yes | Excluded | Yes |  |  |  |
| No. retrieved oocytes | 3 | 5 | 4 | n/a | 11 |  |  |  |
| No. ST oocytes | 2 | Canceled | 4 | n/a | 7 |  |  |  |
| ST blastocysts | 0 | n/a | 2 | n/a | 4 |  |  |  |
| Grade at D6 | n/a | n/a | 5AA | 5BB | n/a | 5AA | 5AA | 5BB | 5CC |
| Aneuploidy | n/a | n/a | Yes:+9 | n/t | n/a | n/t | No | No | No |
| Sex | n/a | n/a | M | n/a | n/a | n/a | M | F | F |
| mtDNA carryover | n/a | n/a | < 1% | n/a | n/a | n/a | < 1% | < 1% | < 1%* |

GENERATION OF HUMAN OOCYTES

CROSS REFERENCE TO RELATED APPLICATIONS

This is a § 371 U.S. national stage of International Application No. PCT/US2017/060720, filed Nov. 8, 2017, which was published in English under PCT Article 21(2), and which claims the benefit of U.S. Provisional Application No. 62/427,546, filed Nov. 29, 2016, and U.S. Provisional Application No. 62/419,638, filed Nov. 9, 2016.

FIELD

Generally, the field involves the generation of human oocytes in vitro by the transfer of nuclear material. More specifically, the field involves generation of human oocytes by nuclear transfer of polar bodies into enucleated donor oocytes and/or the transfer of nuclear material from an oocyte from an oocyte containing mitochondrial DNA mutations to an oocyte lacking such mutations.

BACKGROUND

Infertility attributed to both male and female factors affects millions of families around the world and while the assisted reproductive technologies (ARTS) can circumvent many cases (Huang J Y and Rosenwaks Z, *Meth Mol Biol* 1154, 171-231 (2014); Leridon H, *Human Reproduction* 19, 1548-1553 (2004); Trounson A and Mohr L, *Nature* 305, 707-709 (1983); all of which are incorporated by reference herein), it's efficacy is particularly limited by the number and quality of oocytes that decline with advanced maternal age (Leridon 2004 supra). Therefore, the development of additional sources of competent oocytes, genetically related to patients is desirable.

Perhaps the ultimate approach would involve the differentiation of pluripotent stem cells into primordial germ cells (PGCs) and ultimately into mature oocytes (Daley G Q et al, *Science* 316, 409-410 (2007); Handel M A et al, *Cell* 157, 1257-1261 (2014); Hayashi Y et al, *Fertil Steril* 97, 1250-1259 (2012); Matthews T J et al, *NCHS Data Brief* 1-8 (2009); all of which are incorporated by reference herein). However, the complexity of establishing an in vitro system for producing functional haploid human oocytes currently limits this application (Irie N et al, *Cell* 160, 253-268 (2015) and Sasaki K et al, *Cell Stem Cell* 17, 178-194 (2015); both of which are incorporated by reference herein).

Maternally inherited mtDNA mutations can cause fatal or severe debilitating diseases in children (Archer S L, *N Engl J Med* 369, 2236-2251 (2013); Koopman W J et al, *N Engl J Med* 366, 1132-1141 (2012); and Schon E et al, *Nat Rev Genet* 13, 878-890 (2012); all of which are incorporated by reference herein). Disease severity is dependent on the specific gene mutation and the ratio of pathogenic to wild-type mtDNA (heteroplasmy level) in each cell and tissue (Wallace D C & Chalkia D, *Cold Spr Harb Perspect Biol* 5, a021220 (2013); incorporated by reference herein). Pathogenic mtDNA mutations are relatively common with an estimated 778 affected children born each year in the United States (Gorman G S et al, *N Engl J Med* 372, 885-887 (2015); incorporated by reference herein). Currently, there is no effective cure for patients with mtDNA mutations. Therefore, mitochondrial replacement techniques (MRTs) have been developed to prevent transmission of mutant mtDNA from mothers to their children (Wolf D P et al, *Trends Mol Med* 21, 68-76 (2015); Wang T et al, *Cell* 157, 1591-1604 (2014); Tachibana M et al, *Nature* 493, 627-631 (2013); Craven L et al, *Nature* 465, 82-85 (2010); and Tachibana M et al, *Nature* 461, 367-372 (2009); all of which are incorporated by reference herein). Regulatory agencies in the US and UK are currently evaluating clinical applications of MRT designed to assess efficacy and safety. To date, the clinical aspects of MRT have not been studied including issues of patient eligibility, embryo development and maintenance of donor mtDNA post-MRT.

There remains a need for improved methods of assisting with fertilization, implantation, and successful pregnancies in patients with declining or otherwise incompetent oocytes.

SUMMARY

Provided herein are methods for preparing oocytes for fertilization and uterine implantation.

Disclosed herein is the de novo reconstruction of haploid human oocytes by recycling of PB1 genomes via nuclear transfer into donor cytoplasm (Gurdon J B, *Rambam Maimonides Med J* 6 (2015), incorporated by reference herein).

Oocyte defects lie at the heart of some forms of infertility, and could potentially be addressed therapeutically by alternative routes for oocyte formation. Disclosed herein is the generation of functional human oocytes following nuclear transfer of first polar body (PB1) genomes from metaphase II (MII) oocytes into enucleated donor MII cytoplasm (polar body nuclear transfer, PBNT). The reconstructed oocytes supported the formation of de novo meiotic spindles and, after fertilization with sperm, meiosis completion and formation of normal diploid zygotes. While PBNT zygotes developed to blastocysts less frequently (42%) than controls (75%), genome-wide genetic, epigenetic and transcriptional analyses of PBNT and control embryonic stem cells (ESCs) indicated comparable numbers of structural variations and markedly similar DNA methylation and transcriptome profiles. PB1 genetic material via introduction into donor cytoplasm can provide oocytes for infertility treatment or mitochondrial replacement therapy for mtDNA disease.

This method allows generating additional patient-matched oocytes for treatment infertility. By utilizing each patient MII oocyte and its PB1 (plus donor cytoplasm), patient-related oocytes/embryos can be theoretically doubled. Realistically, the development of PBNT embryos to blastocysts is lower. So one can estimate that the number of viable embryos for transfer and thus pregnancy rates can increase by 40%.

Disclosed herein is a method of generating a viable human oocyte. The method involves enucleating a first oocyte at the MII stage, thereby creating a cytoplast, isolating a polar body from a second oocyte by aspiration, and placing the polar body into the perivitelline space of the cytoplast. The method can also involve fertilizing the viable human oocyte, thereby creating an embryo. The method can further comprise implanting the embryo in a receptive uterine (endometrial) lining. Enucleating the first oocyte can be performed in a medium comprising at least 10% human tubal fluid, a buffer, and cytochalasin B using a Polarized Microscope Imaging System. Isolating the polar body can be performed in a medium comprising at least 10% human tubal fluid, buffer, cytochalasin B, and fusion with the donor cytoplast can be induced with HVJ-E (hemagglutinating virus of Japan/Sendai virus envelope) extract.

Provided is a method for preparing an oocyte for fertilization, the method comprising the steps of:
a) isolating a first oocyte containing a polar body;
b) gaining access through the zona pellucida of the first oocyte;
c) removing the polar body from the first oocyte;
d) removing the nuclear spindle from a second oocyte to create an enucleated cytoplast;
e) placing the polar body removed from the first oocyte into the perivitelline space of the enucleated cytoplast.

Also provided is a method of producing a human oocyte in vitro, the method comprising:
a) determining a mitochondrial DNA sequence of the conserved sequence box II of a donor oocyte;
b) enucleating the donor oocyte while the donor oocyte is arrested at metaphase II, thereby isolating donor nuclear genetic material;
c) introducing the donor nuclear genetic material into an enucleated recipient oocyte, provided that the mitochondrial DNA of the donor oocyte has the same conserved sequence box II genotype as the recipient oocyte.

Additional embodiments of both methods above involve an additional step of fertilizing the newly created oocyte through in vitro fertilization. In additional embodiments, the fertilized oocyte/embryo is cultured to the blastocyst stage before implantation in a receptive uterus/endometrial lining.

Figure 6A:
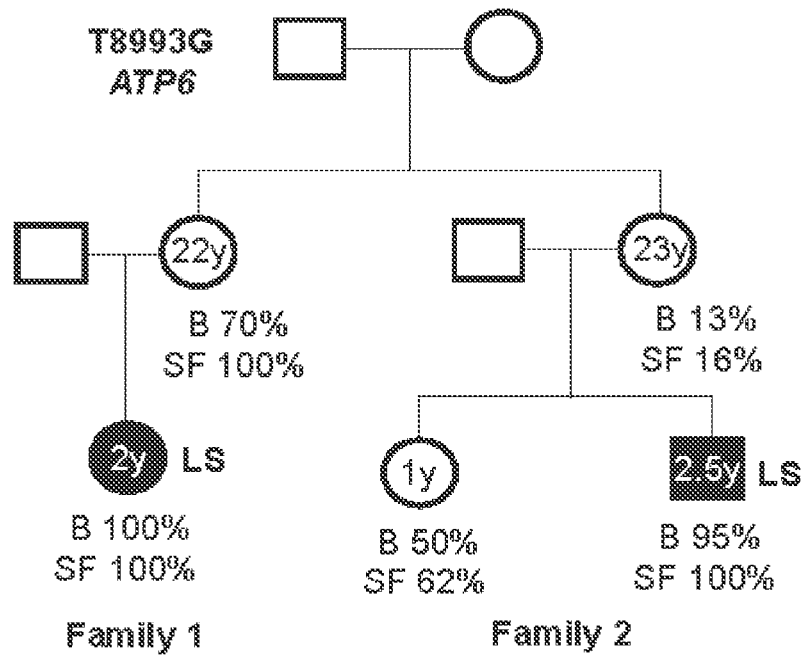
FIG. 6A is a pedigree of Leigh Syndrome families 1 and 2.
Figure 6B:
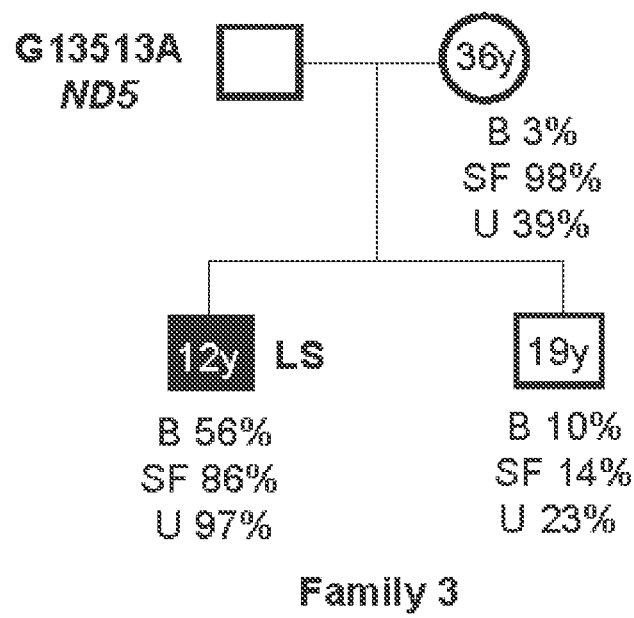
FIG. 6B is a pedigree of Leigh Syndrome G13513A family 3.
Figure 6C:
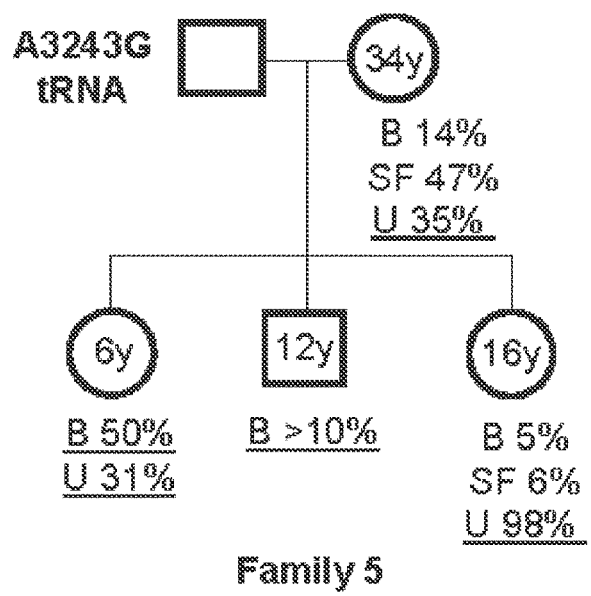
FIG. 6C is a pedigree of MELAS syndrome A3243G family 5 from large pedigree (see also FIG. 10B).

For all of FIGS. 6A, 6B, and 6C, the underlined heteroplasmy levels were obtained from previous reports. In all families, the heteroplasmy levels for mtDNA mutations were diverse among tissues and individuals, and associated with clinical disease. Black filled, diagnosed as a mitochondrial disease. LS=Leigh syndrome. y=year-old. Square=male; circle=female. B=blood; SF=skin fibroblasts; U=urine.

Figure 7A:
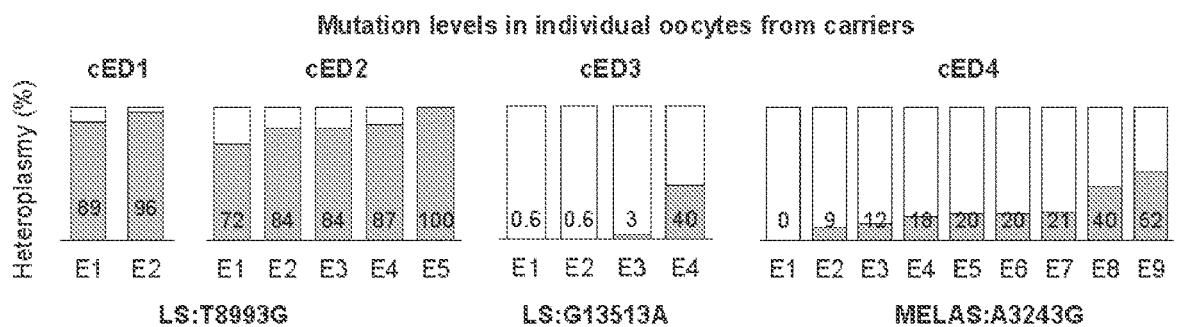

FIG. 7A is a set of graphs showing individual oocytes harboring different heteroplasmy levels. cED=carrier oocyte donor.

Figure 7B:
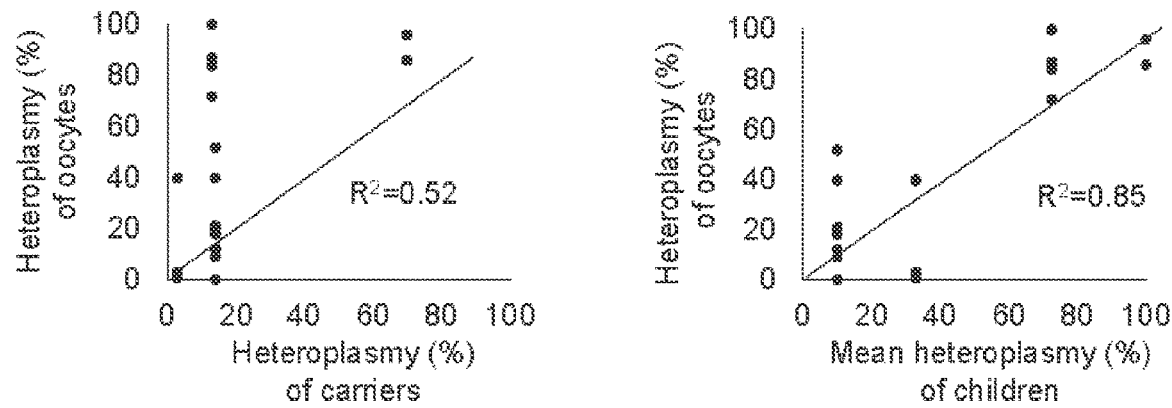

FIG. 7B is a set of two plots showing the average heteroplasmy level in oocytes correlated to levels in existing children rather than those in carrier oocyte donors. Heteroplasmy levels of carriers and children were measured in blood. R=Pearson's r values.

Figure 7C:
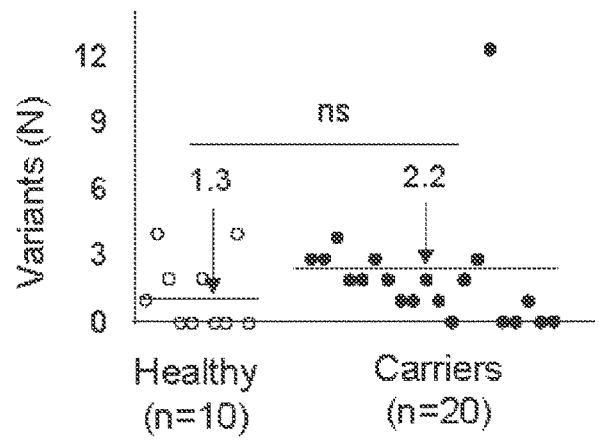

FIG. 7C is a plot showing comparable mtDNA variants between oocytes with healthy mtDNA and those carrying mtDNA mutations (p>0.05).

Figure 7D:
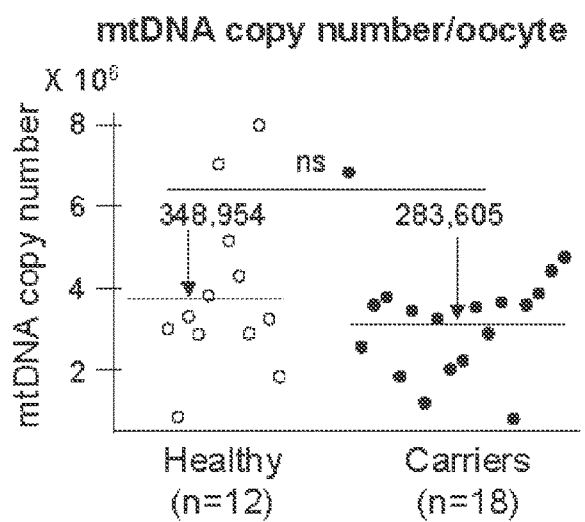

FIG. 7D is a plot showing that the total copy number of mtDNA was comparable in oocytes with healthy mtDNA and those carrying pathogenic mtDNA (p>0.05). Karyoplasts were isolated from carrier oocytes for ST except oocytes from cED2, which exhibited premature luteinization. Oocytes from healthy egg donors were mature MII. n=the number of oocytes. LS: Leigh syndrome; MELAS: mitochondrial encephalomyopathy with lactic acidosis and stroke-like episodes. t-test, ns=not significant (p>0.05).

Figure 8A:
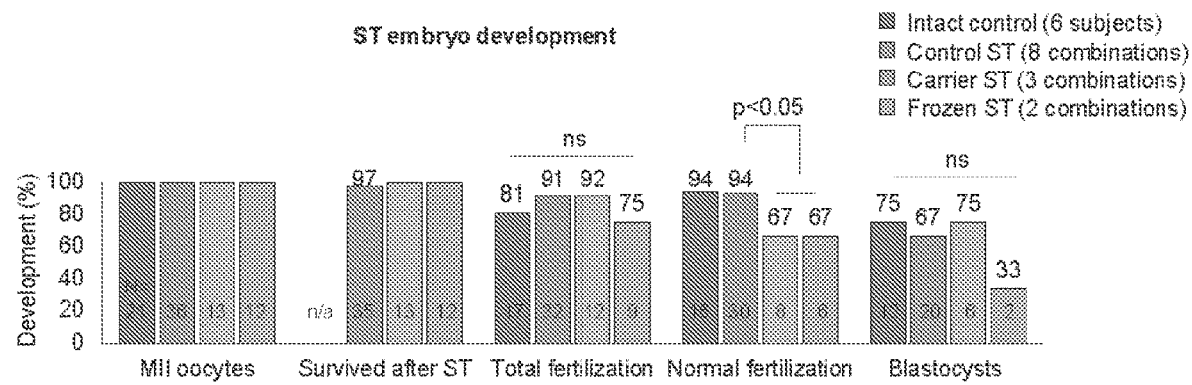

FIG. 8A is a set of graphs showing ST embryo development following various experimental manipulations. Similar developmental outcomes were observed among groups except normal fertilization rate, which was significantly lower in carrier and frozen ST groups (p<0.05). Combinations=mixture of different mtDNA haplotypes between karyoplast and cytoplast; Intact control=non-manipulated, ICSI only.

Figure 8B:
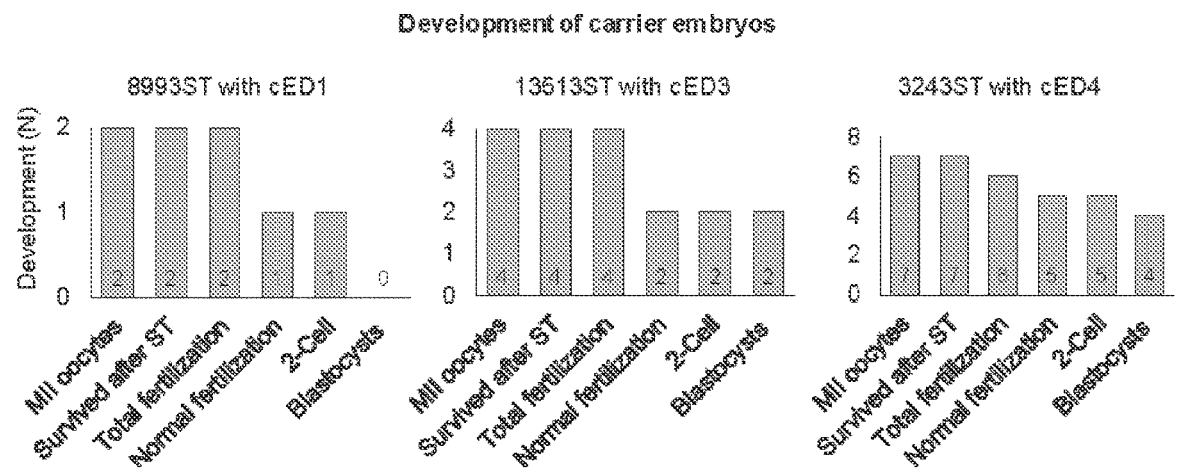

FIG. 8B is a set of graphs showing that carrier ST embryos from different mutation types showed a similar development pattern.

Figure 8C:
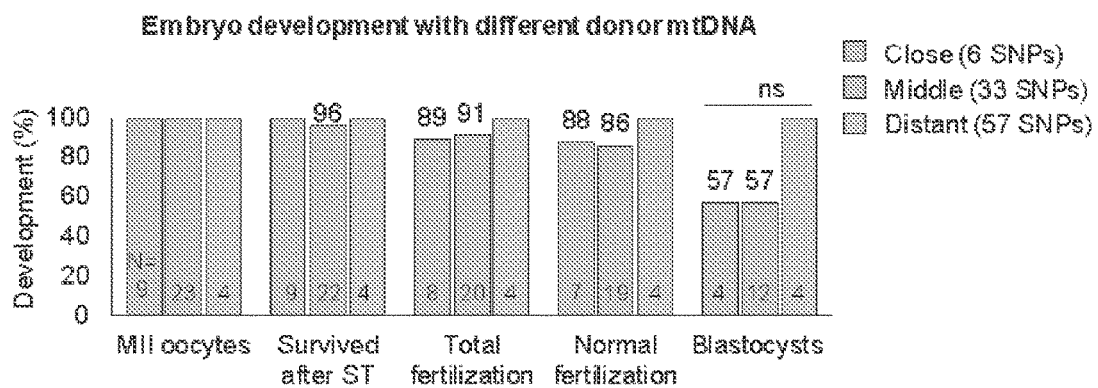

FIG. 8C is a set of graphs showing control ST embryo development as a function of donor mtDNA matching distances. The numbers on the top of bars are percentage (%) of embryo development. N=the number of embryos. ns=not significant (p>0.05).

Figure 8D:
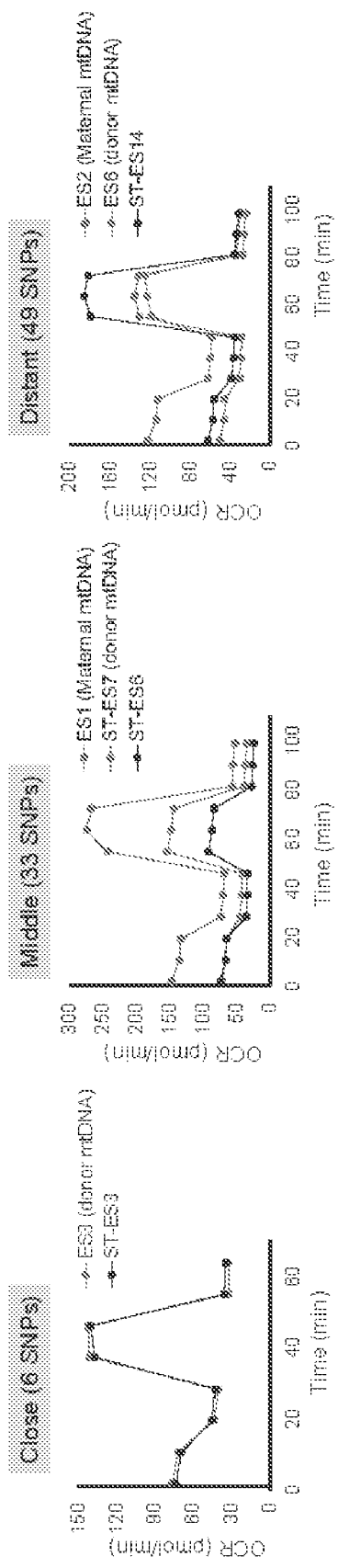

FIG. 8D is a set of plots of NPCs derived from ST ESCs with 6 and 49 SNP differences in donor mtDNA displayed oxygen consumption rates (OCR) similar to non-manipulated controls. However, NPCs with 33 SNPs showed significantly reduced OCR than controls with either donor or maternal mtDNA (p<0.05). Seahorse assay was repeated 3 different times with 6 to 18 replicates each time. See also FIG. 13A. NPCs=neural progenitor cells. SNPs=single nucleotide polymorphisms. t-test or One-way ANOVA.

Figure 9A:
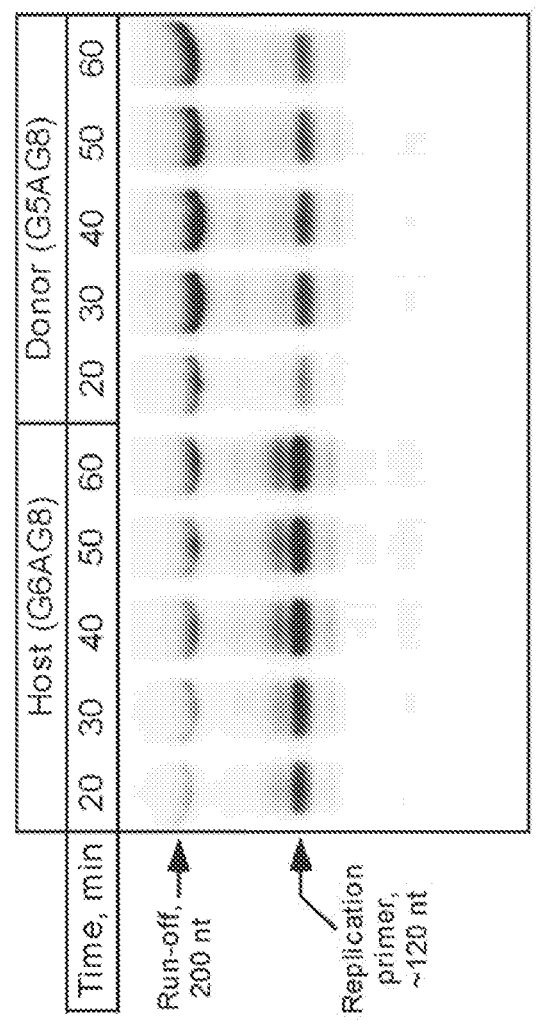

FIG. 9A is an image of a gel showing polymorphism in the CSBII region of donor mtDNA results in a decreased efficiency of replication primer generation by mitochondrial RNA polymerase. The 311-315CCCCC polymorphism is a shortening of the first G-stretch in the G-quadruplex region of mtDNA (G5 vs. G6 stretch), responsible for transcription termination and replication primer generation in human mitochondria.

Figure 9B:
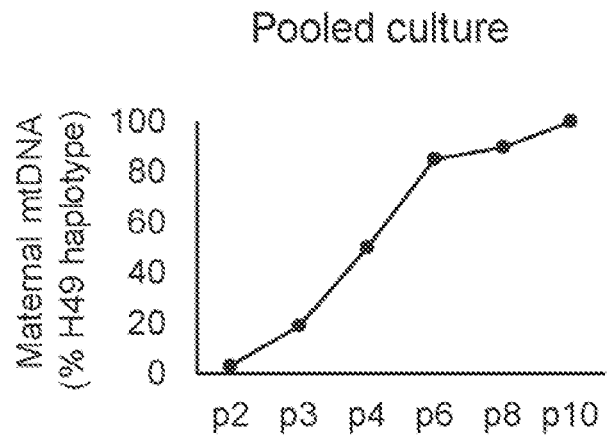

FIG. 9B is a plot showing heteroplasmy rates for the maternal mtDNA (H49 haplotype) gradually increased during in vitro extended culture of 3243ST-ES1 and reached homoplasmy.

Figure 9C:
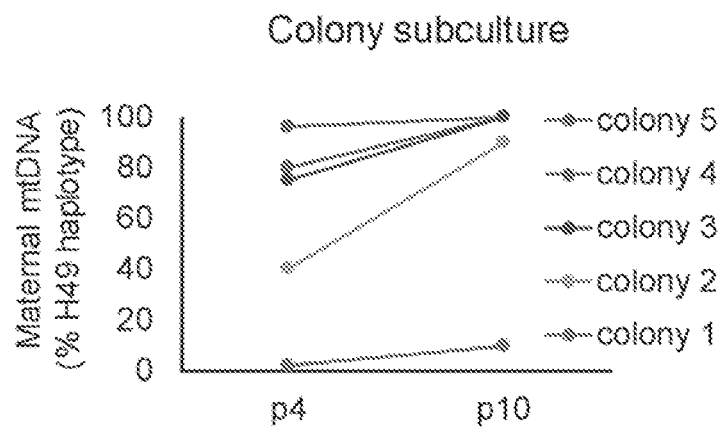

FIG. 9C is a plot showing that the heteroplasmy levels also increased during single ESC colony subculture.

Figure 9D:
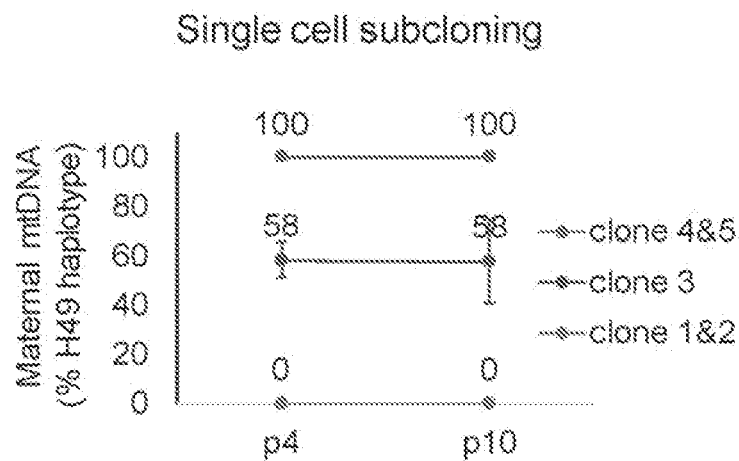

FIG. 9D is a plot showing the maintenance of stable heteroplasmy in progeny of individually cultured cells.

Figure 9E:
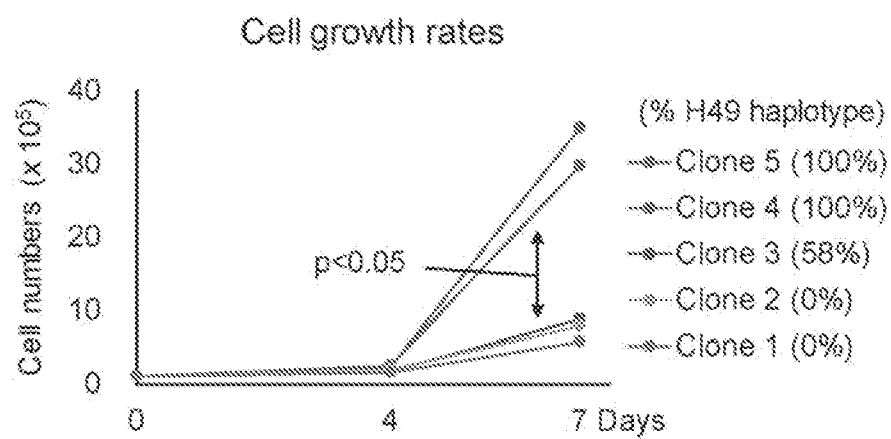

FIG. 9E is a plot showing faster cell growth and proliferation rates in clones containing higher maternal mtDNA heteroplasmy.

Figure 9F:
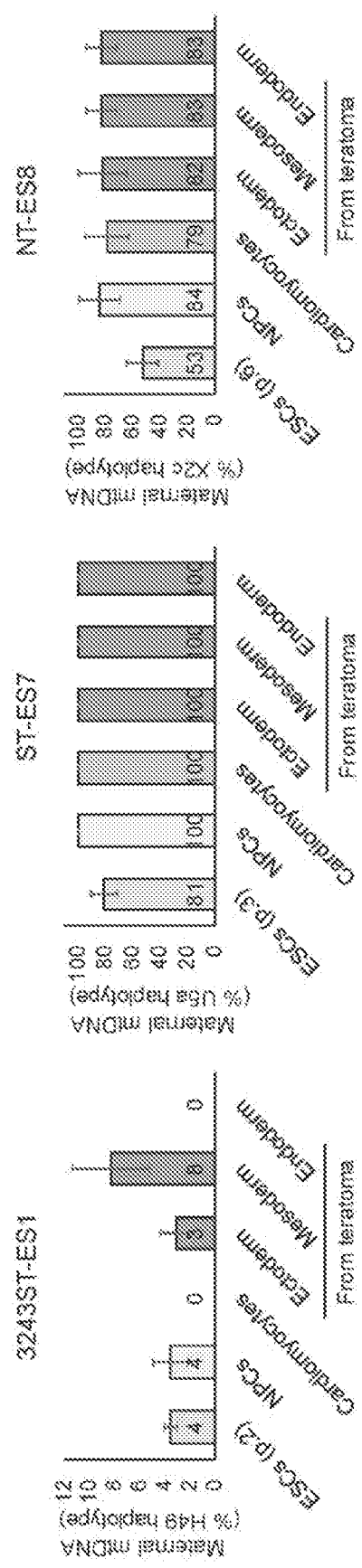

FIG. 9F is a set of three graphs showing maternal mtDNA heteroplasmy changes in reversed cell lines 3243ST-ES1, ST-ES7 and NT-ES8 during in vitro and in vivo differentiation. One-way ANOVA. Mean±SD.

FIG. 10A is a table showing families with mitochondrial disease and reproductive age women recruited for MRT. All LS families had an existing, severely affected child. F, family; non-syn, non-synonymous; n/a, non-applicable.

FIG. 10B shows that Family 5 was selected from an extensive MELAS syndrome pedigree. Clinical phenotypes of A3243G MELAS syndrome varied even with similar heteroplasmy levels. Squares, males vs. Circles, females; B=blood and U=urine. n/t, non-tested. *, the first MELAS patient diagnosed clinically. Heteroplasmy in blood (upper) and urine (lower).

Figure 11A:
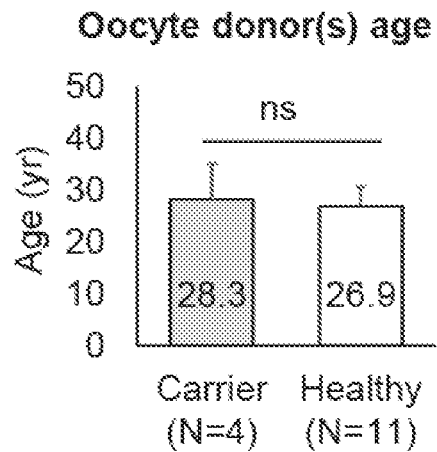

FIG. 11A is a graph showing that the age of oocyte donors was similar between carrier and healthy groups.

Figure 11B:
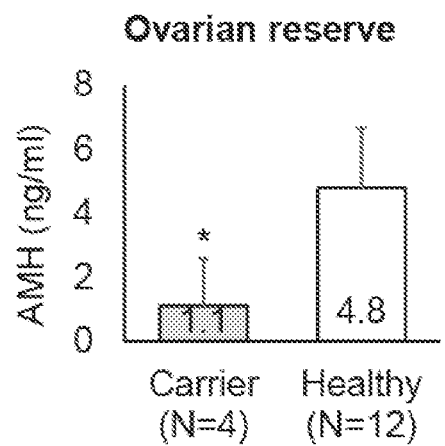

FIG. 11B is a graph showing that ovarian reserve was significantly lower in carriers relative to healthy oocyte donors.

Figure 11C:
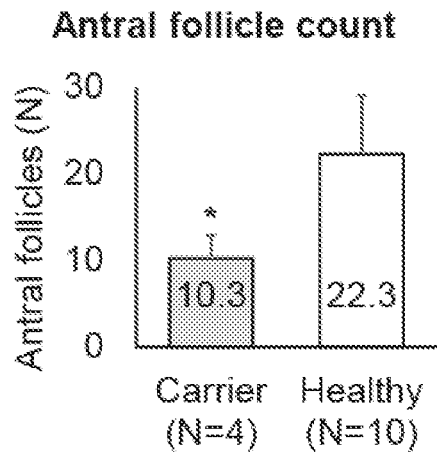

FIG. 11C is a graph showing that antral follicle count (AFC) was significantly lower in carriers relative to healthy oocyte donors.

Figure 11D:
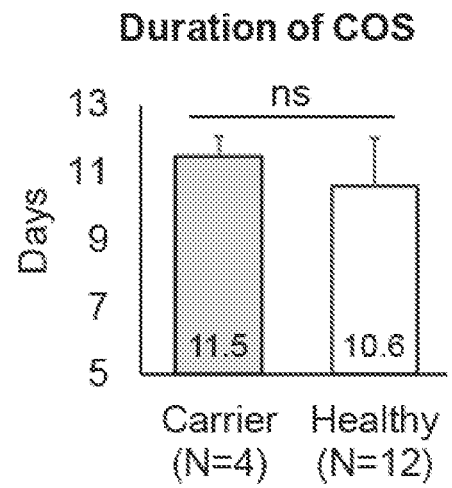

FIG. 11D is a graph showing that the duration of COS was longer in carriers.

Figure 11E:
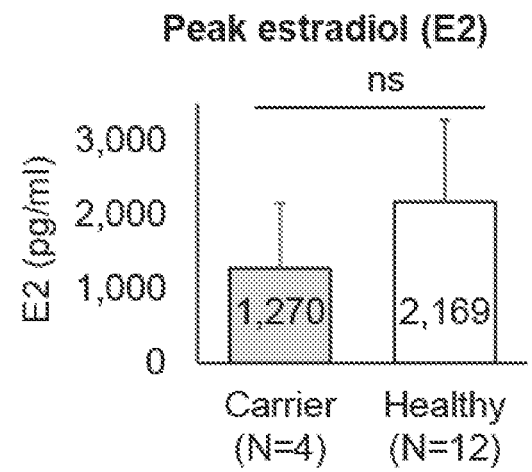

FIG. 11E is a graph showing that peak estradiol (E2) on the day of hCG trended lower in carriers.

Figure 11F:
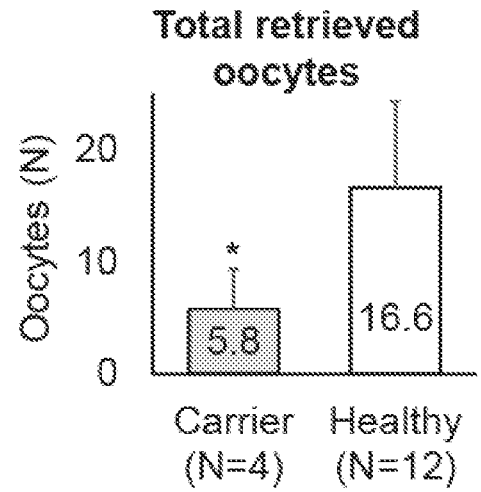

FIG. 11F is a graph showing that the total oocyte yield was significantly lower in carriers than healthy oocyte donors.

Figures 11G, 11H:
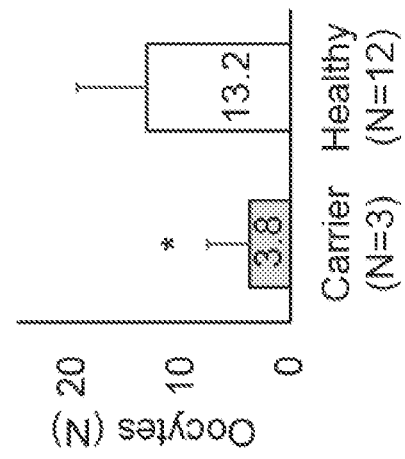

FIG. 11G is a graph showing that the number of mature oocytes was significantly lower in carriers than healthy oocyte donors.

FIG. 11H is a table of baseline characteristics and cycle outcomes. Carriers had higher BMI and lower AMH levels. Lower peak estradiol levels were measured in cED1 and cED2. Birth control method: combined oral contraceptive. Medroxyprogesterone.

Figure 11I:
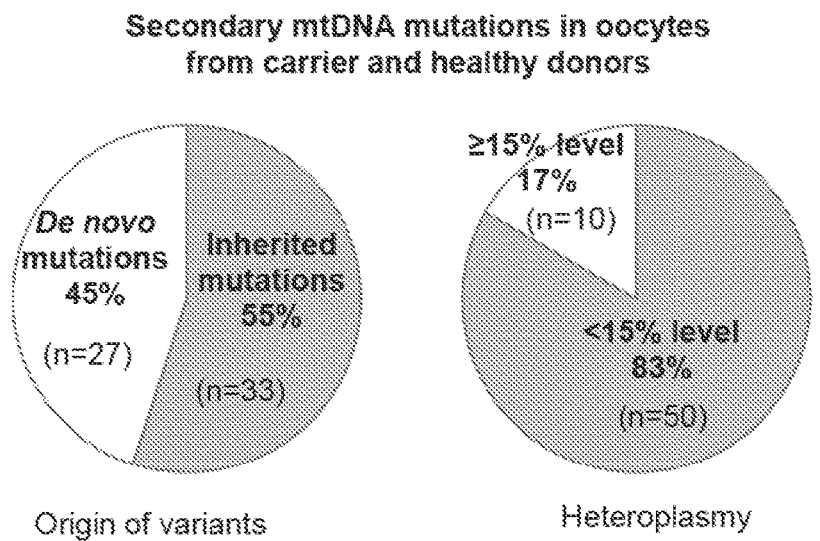

FIG. 11I is a set of two pie charts showing Analysis of heteroplasmic mtDNA variants detected in MII oocytes. De novo indicates unique mutations found in individual oocytes; inherited means mutations shared with other oocytes, sibling children or egg donors. n=the number of mutations in individual oocytes.

Figure 11J:
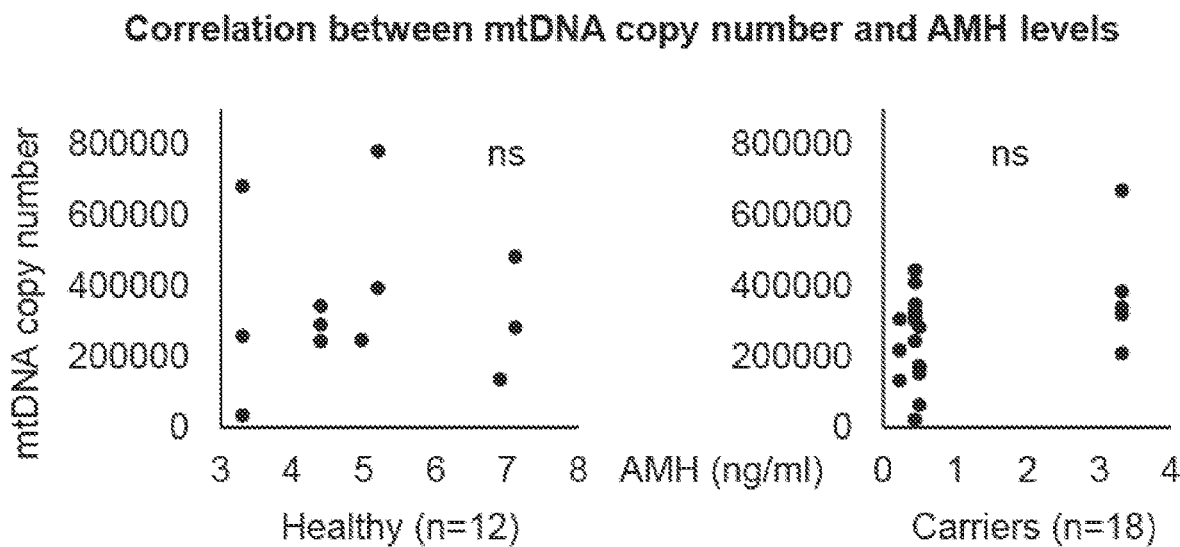

FIG. 11J is a set of two plots showing that AMH levels, a measure of ovarian reserve, were not correlated with mtDNA copy number. n=the number of oocytes. ns=not significant.

FIG. 12A is a table showing the results of whole mtDNA sequencing performed to identify haplotypes of all egg donors and ST was performed to match various haplotypes. Cyto, cytoplast; Karyo, karyoplast.

FIG. 12B is a set of images showing normal fertilization (2PN, left) and abnormal fertilization (1 or 3 PN). See arrows.

FIG. 12C is a table showing carrier ST showed higher abnormal fertilization than controls. One 3 PN zygote from control ST group developed to a blastocyst and displayed a 69, XXY karyotype. * p<0.05.

FIG. 12D is a table showing that the blastulation rate was similar between vitrified cytoplasm with fresh spindles and vitrified spindles with fresh cytoplasm (p>0.05).

FIG. 12E is a set of graphs showing embryo development with different donor mitochondrial DNA.

Figure 13A:
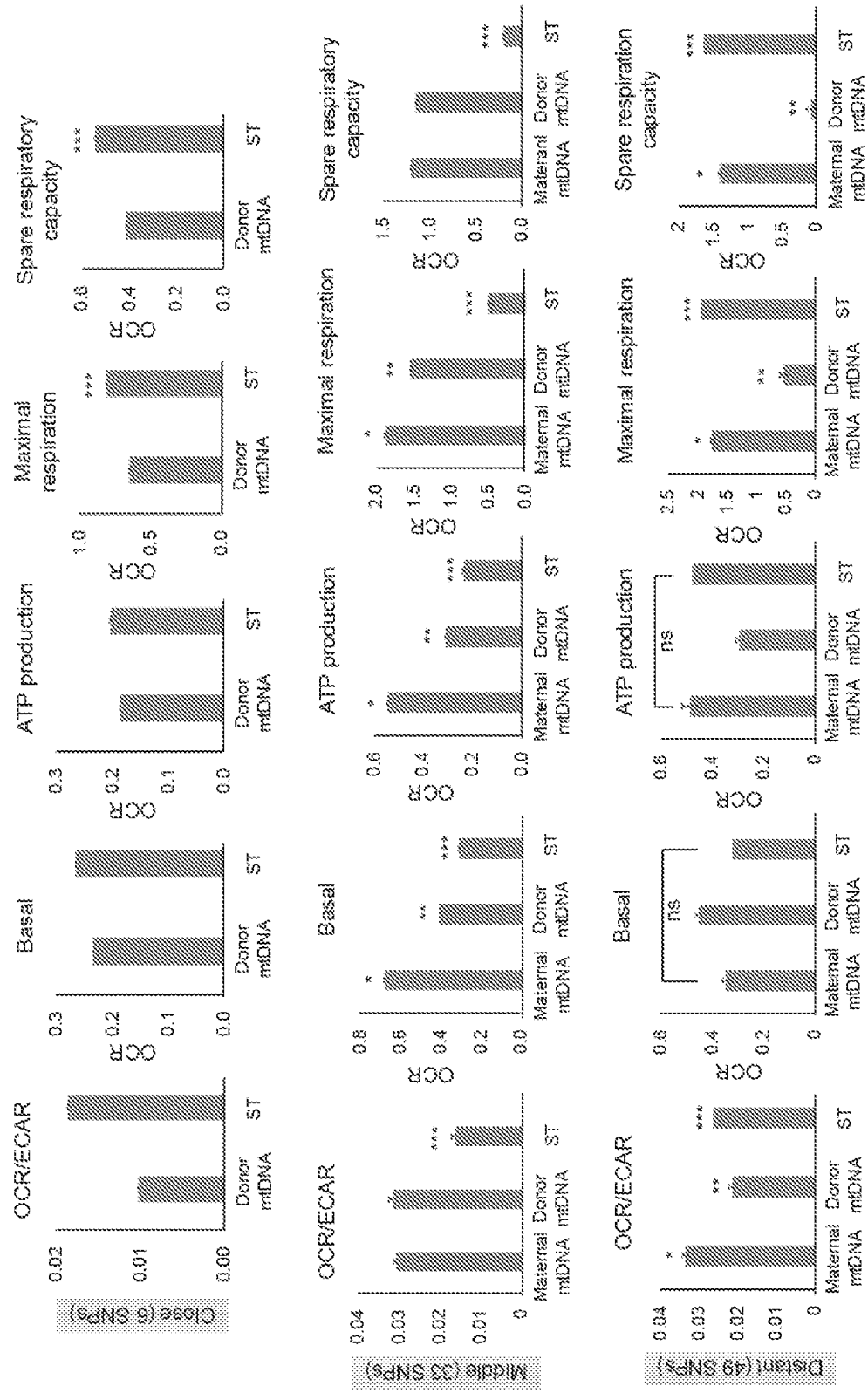

FIG. 13A is a set of 15 graphs showing the results where energy metabolism (OCR/ECAR) was measured and compared between neural progenitor cells (NPCs) derived from MRT and control embryos carrying either donor or maternal mtDNA. OCR=oxygen consumption rate (representing OXPHOS), ECAR=extracellular acidification rate (representing glycolysis). NPCs from MRT ESCs with 6 and 49 SNP differences displayed comparable OCR to NPCs harboring maternal or donor mtDNA except maximal respiration in 49 SNP group. OCR was reduced in NPCs with 33 SNPs. The OCR data was normalized by live cell DNA content. *vs. host mtDNA, vs. donor mtDNA, *vs. ST ($p<0.05$, t-test or one-way ANOVA, n=16-18 technical replicates). Mean±SEM.

FIG. 13B is a set of graphs showing mitochondrial respiratory chain enzyme activity in differentiated cells from ST-ESCs. Mitochondrial Complex I and IV activities in differentiated cells from ST-ESCs carrying donor mtDNA with 49 SNP differences were comparable to controls with either donor or maternal mtDNA.

FIG. 14A is a table showing a summary of in vitro and in vivo differentiation of ESCs derived from ST or SCNT embryos carrying donor mtDNA. Similar to control IVF-ESCs, all tested MRT ESCs produced teratoma tumors in vivo and formed neural progenitor cells (NPCs) and cardiomyocytes in vitro.

Figures 14B, 15A:
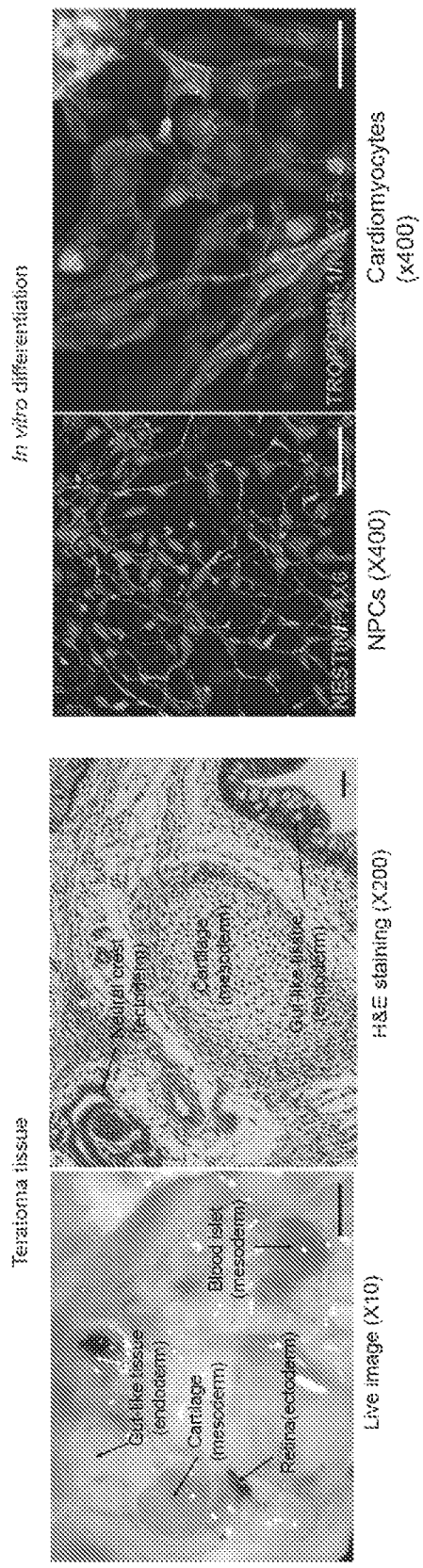

FIG. 14B is a histological analysis of differentiated tissues from MRT-ESCs. The representative tissues were collected and used for mtDNA carryover analysis and measurements of mitochondrial function.

FIG. 15A is a graph and table showing that the aneuploidy rate in blastocysts determined by array CGH was not significantly different in ST groups compared to control.

FIG. 15B is a graph and table showing that a Karyotype abnormality rate in ESCs determined by G-banding analysis was also comparable among ST groups. Bars=mean±s.d. Number inside bars=the number of blastocysts or ESC lines. Simple $\chi 2$ tests.

Figure 16A:
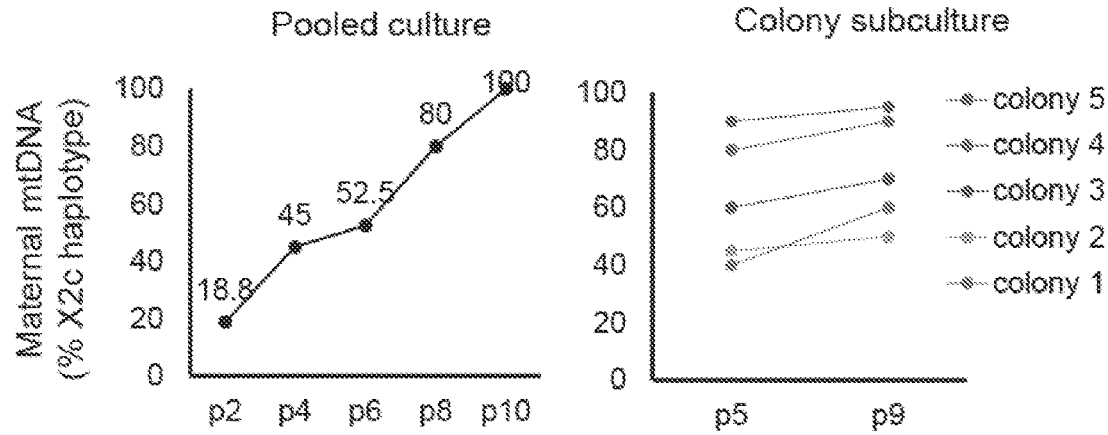

FIG. 16A is a set of two plots showing maternal mtDNA (X2c haplotype) heteroplasmy increased during extended in vitro culture and reached homoplasmy in pooled cultures or in individual colony subcultures.

Figure 16B:
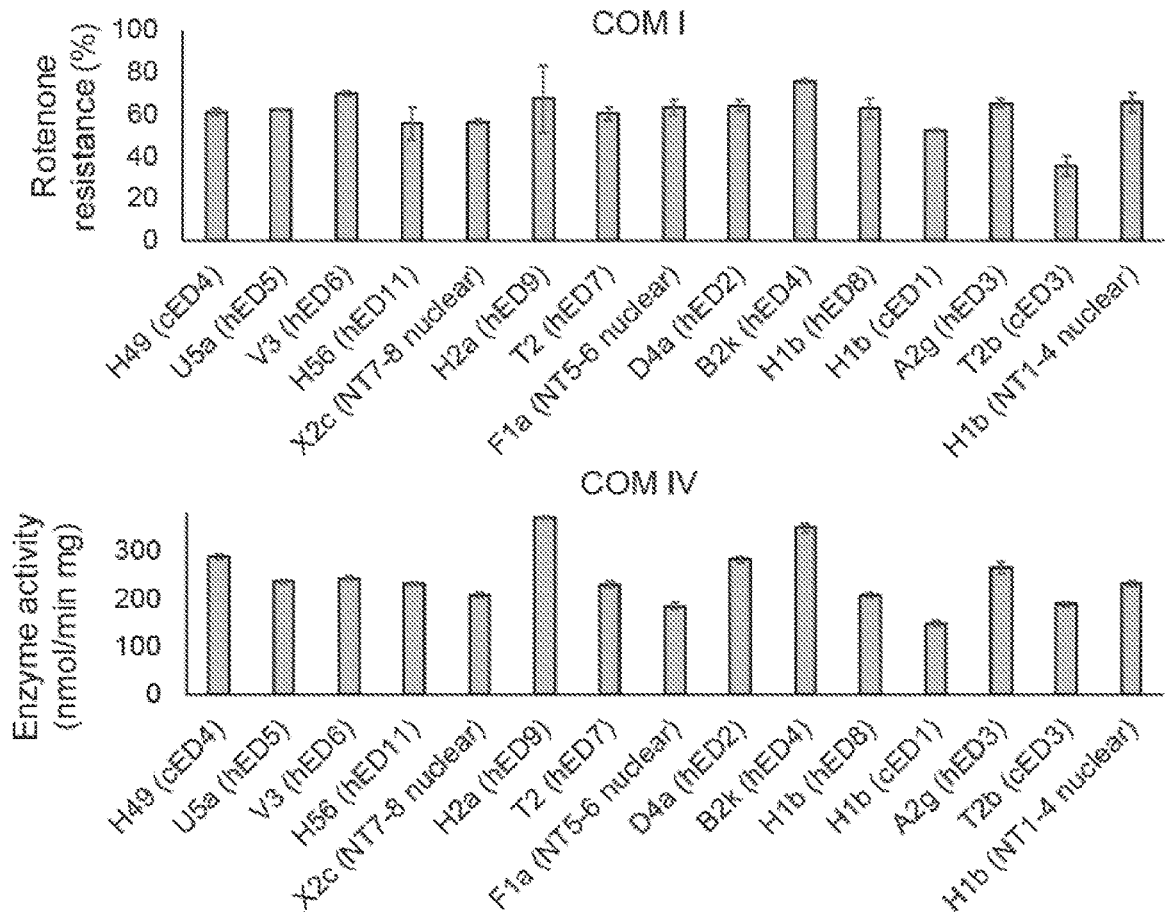

FIG. 16B is a set of two graphs showing respiratory chain complex 1 (COM I) and complex 4 (COM IV) enzyme activities were measured in fibroblasts carrying various human mtDNA haplotypes used in this study. No significant differences were noted.

FIG. 17 is a table summarizing array CGH in intact and ST blastocysts.

FIG. 18 is a table summarizing G-banding of ESC lines derived from control and ST blastocysts.

DETAILED DESCRIPTION

Provided herein is a method of generating a viable human oocyte, the method comprising the steps of:
  a) enucleating a first oocyte at the MII stage, thereby creating a cytoplast;
  b) isolating a polar body from a second oocyte by aspiration; and
  c) placing the polar body into the perivitelline space thereby fusing the polar body with the cytoplast and generating the viable human oocyte.

In other embodiments, the methods herein involving polar body transplantation further comprise a step of fertilizing the viable human oocyte via in vitro fertilization, thereby creating an embryo. In further embodiments, the method further comprises implanting the embryo in a receptive endometrial uterine lining.

In other embodiments of the methods, enucleating the first oocyte is performed in a medium comprising at least 10% human tubal fluid, HEPES buffer, and cytochalasin B. In other embodiments the enucleation step is completed using a Polarized Microscope Imaging System.

In still further embodiments, the method step for isolating the polar body is performed in a medium comprising at least 10% human tubal fluid, HEPES buffer, cytochalasin B, and fusion with donor cytoplast induced with HVJ-E extract.

In other embodiments, the zona pellucida is opened via methods selected from zona cutting, laser drilling (such as with a compact nitrogen laser), and acid drilling (such as with acidic Tyrode's medium).

Also provided is a method of producing a human oocyte in vitro, the method comprising:
  a) determining a mitochondrial DNA sequence of the conserved sequence box II of a donor oocyte;
  b) enucleating the donor oocyte while the donor oocyte is arrested at metaphase II, thereby isolating donor nuclear genetic material;
  c) introducing the donor nuclear genetic material into an enucleated recipient oocyte, provided that the mitochondrial DNA of the donor oocyte has the same conserved sequence box II genotype as the recipient oocyte.

In some embodiments, the method immediately above is accomplished where the donor oocyte and the recipient oocyte both have the G5A8 genotype or both have the G6A8 genotype. In still other embodiments of the method the mitochondrial DNA from the donor oocyte comprises a mutation that results in a mitochondrial disease, including but not limited to Leigh Syndrome or MELAS.

Also provided is a method of producing a human oocyte in vitro, the produced human oocyte comprising minimal maternal mitochondrial DNA, and the method comprising the steps of:
  a) determining the sequence of the major non-coding region of the mitochondrial DNA of a donor oocyte, where the major non-coding region sequence includes a D loop region;
  b) enucleating the donor oocyte while the donor oocyte is arrested at metaphase II, thereby isolating donor nuclear genetic material; and
  c) introducing the donor nuclear genetic material into an enucleated recipient oocyte, provided that the mitochondrial DNA of the donor oocyte has the same major non-coding region sequence as the recipient oocyte.

In further embodiments of the method immediately above the donor oocyte and the recipient oocyte both have the H56, H1b, U5a, F1a, X2c, D4a, H49, or B2k mtDNA haplotype. In other embodiments, the mitochondrial DNA from the donor oocyte comprises a mutation that results in a mitochondrial disease, such as Leigh Syndrome or MELAS.

Other mitochondrial diseases for which use of the present methods may be considered include, but are not limited to, possible occurrence of mitochondrial myopathy; diabetes mellitus and deafness; progressive infantile poliodystrophy (Alpers disease); Leber's hereditary optic neuropathy; Barth Syndrome/Lethal Infantile Cardiomyopathy (LIC); neuropathy, ataxia, retinitis pigmentosa, and ptosis (NARP); myoneurogenic gastrointestinal encephalolpathy (MNGIE); carnitine-acyl-carnitine deficiency; carnitine deficiency; creatine deficiency syndromes; Co-enzyme Q10 deficiency; Complex I deficiency; Complex II deficiency; Complex III deficiency; Complex IV deficiency/COX deficiency; Complex V deficiency; myoclonic epilepsy with ragged red fibers (MERRF); mitochondrial myopathy, encephalomyopathy, lactic acidosis, stroke-like-symptoms (MELAS); mtDNA depletion; Chronic Progressive External Ophthalmoplegia Syndrome (CPEO); CPT I Deficiency; CPT II Deficiency; Kearns-Sayre Syndrome (KSS); lactic acidosis; LBSL-Leukodystrophy; Long-Chain Acyl-CoA Dehydrogenase Deficiency (LCAD); LCHAD; Luft Disease; Multiple Acyl-CoA Dehydrogenase Deficiency; Short-Chain Acyl-CoA Dehydrogenase Deficiency; Medium-Chain Acyl-CoA Dehydrogenase Deficiency; Very Long-Chain Acyl-CoA Dehydrogenase Deficiency; Mitochondrial Encephalomyopathy Lactic Acidosis and Stroke-like Episodes (MELAS); Mitochondrial Recessive Ataxia Syndrome; Mitochondrial Cytapathy; Mitochondrial DNA Depletion; Mitochondrial encephalopathy; Myoneurogastrointestinal Disorder and Encephalopathy; Pearson Syndrome; Pyruvate Carboxylase Deficiency; Pyruvate Dehydrogenase Deficiency; and POLG2 Mutations.

Definitions

The term "polar body" refers to haploid cells, significantly smaller than an oocyte that is formed in conjunction with an oocyte during oogenesis. In particular, polar bodies include the half of the diploid chromosome set not included in the oocyte after meiotic division. Polar bodies comprise polynucleotides (e.g., DNA) that encode information about the individual. Nuclear genetic material includes, but is not limited to, chromosomes and chromatin. The term includes nuclear genetic material produced by meiotic cell division such as the division or a diploid cell to a haploid oocyte. Thus, a cell includes nuclear genetic material derived from a donor polar body if the polar body has been transferred into an enucleated cytoplast via somatic cell nuclear transfer.

The term "oocyte" refers to a female gamete or germ cell involved in reproduction, also called an egg. A mature oocyte is a haploid cell with a single set of maternal chromosomes (23, X in a human primate) and is halted at metaphase II. A "hybrid" oocyte has the cytoplasm from a first primate oocyte (termed a "recipient") but does not have the nuclear genetic material of the recipient; it has the nuclear genetic material from another oocyte or a polar body and is termed a "donor" oocyte.

Meiosis is a process of reductional division in which the number of chromosomes per cell is halved. In animals, meiosis always results in the formation of gametes. During meiosis, the genome of a diploid germ cell, which is composed of long segments of DNA packaged into chromosomes, undergoes DNA replication followed by two rounds of division, resulting in four haploid cells. Each of these cells contain one complete set of chromosomes, or half of the genetic content of the original cell. Meiosis I separates homologous chromosomes, producing two haploid cells (23 chromosomes, N in humans), so meiosis I is referred to as a reductional division. A regular diploid human cell contains 46 chromosomes and is considered 2N because it contains 23 pairs of homologous chromosomes. However, after meiosis I, although the cell contains 46 chromosomes it is only considered N because later in anaphase I the sister chromatids will remain together as the spindle pulls the pair toward the pole of the new cell. In meiosis II, an equational division similar to mitosis occurs whereby the sister chromatids are finally split, creating a total of 4 haploid cells (23 chromosomes, N) per daughter cell from the first division.

A "meiotic spindle" is a structure that separates the chromosomes into daughter cells during meiotic cell division. It is part of the cytoskeleton in eukaryotic cells. The spindle apparatus includes the spindle microtubules, associated proteins, and any centrosomes or asters present at the spindle poles. The spindle apparatus is vaguely ellipsoid in shape and tapers at the ends but spreads out in the middle. In the wide middle portion, known as the spindle midzone, antiparallel microtubules are bundled by kinesins. At the pointed ends, known as spindle poles, microtubules are nucleated by the centrosomes in most animal cells.

The term "mitochondrial DNA" or "mtDNA" refers to the DNA of the mitochondrion, a structure situated in the cytoplasm of the cell rather than in the nucleus (where all the other chromosomes are located). In vivo, all mtDNA is inherited from the mother. There are 2 to 10 copies of the mtDNA genome in each mitochondrion. Mitochondrial DNA is a double-stranded, circular molecule. It is very small relative to the chromosomes in the nucleus and includes only a limited number of genes, such as those encoding a number of the subunits in the mitochondrial respiratory-chain complex and the genes for some ribosomal RNAs and transfer RNAs. A cell includes mtDNA derived from the continued replication cytoplasmically based mitochondria, which in the case of polar body transfer are based in the recipient cytoplast.

The term "DNA methylation" refers to the postsynthetic addition of methyl groups to specific sites on DNA molecules; the reaction is catalyzed by enzymes called DNA methyltransferases that are specific for nucleotide and position of methylation. In eukaryotes, methylation is involved in gene expression, and plays a role in a variety of epigenetic mechanisms, including development, X chromosome inactivation, genomic imprinting, mutability of DNA, and uncontrolled cell growth in cancer.

The term "X chromosome inactivation" refers to the inactivation of one of each pair of X chromosomes to form the Barr body in female mammalian somatic cells. Thus tissues whose original zygote carried heterozygous X borne genes should have individual cells expressing one or other but not both of the X encoded gene products. The inactivation is thought to occur early in development and leads to mosaicism of expression of such genes in the body.

The phrase "dosage compensation" refers to a mechanism that senses gene dosage and regulates expression accordingly. In mammals there is monoallelic expression of X-linked genes that differ in dose between females (XX) and males (XY). "XIST" refers to a gene encoding a large non-coding RNA which has been shown to be necessary for developmentally regulated X chromosome silencing in females. The XIST RNA is about 18 kb and is not translated, it is spliced, and polyadenylated. It is also organized into blocks of repetitive sequence. In vivo, XIST RNA is found to be stably associated with the silenced X chromosome. The expression of XIST RNA is always cis-limited, and is associated with the silenced X chromosome in females.

The term "effective amount" or "therapeutically effective amount" refers to the amount of agent or a cell that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount of a cell or an agent sufficient to reduce or eliminate a symptom of a disease. In another embodiment, a therapeutically effective amount is an amount sufficient to overcome the disease itself.

As used herein, the term "embryo" refers generally to a cellular mass obtained by one or more divisions of a zygote or an activated oocyte with an artificially reprogrammed nucleus. A "morula" is the preimplantation embryo 3-4 days after fertilization, when it is a solid mass, generally composed of 12-32 cells (blastomeres). A "blastocyst" refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst is generally a sphere made up of a layer of cells (the trophectoderm), a fluid-filled cavity (the blastocoel or blastocyst cavity), and a cluster of cells on the interior (the ICM).

"Nuclear transfer" refers to the insertion of a donor polar body nucleus into an enucleated recipient host cell.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Amounts that are "about" a given numeric range or value include the exact numeric range or value. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The development of normal, competent, haploid oocytes depends on two consecutive meiotic cell divisions in the absence of an intermediate DNA replication S-phase (Petronczki et al., 2003). In mammals, primordial germ cells form primary oocytes that undergo chromosome recombination during fetal development and then arrest at prophase of meiosis I. Meiosis is resumed, in turn, in selected primary oocytes after puberty, during periodic menstrual cycles, leading to completion of the first meiotic division, abstriction of PB1 and formation of a secondary oocyte that arrests again at metaphase of meiosis II. MII resumes post-ovulation, during fertilization, resulting in segregation of second polar body (PB2) and the formation of a haploid oocyte genome (Clift D and Schuh M, *Mol Cell Biol* 14, 549-562 (2013); incorporated by reference herein). Haploid DNA contributions from sperm and egg intermingle during preparation for the first mitotic division and completion of fertilization.

Figure 1A:
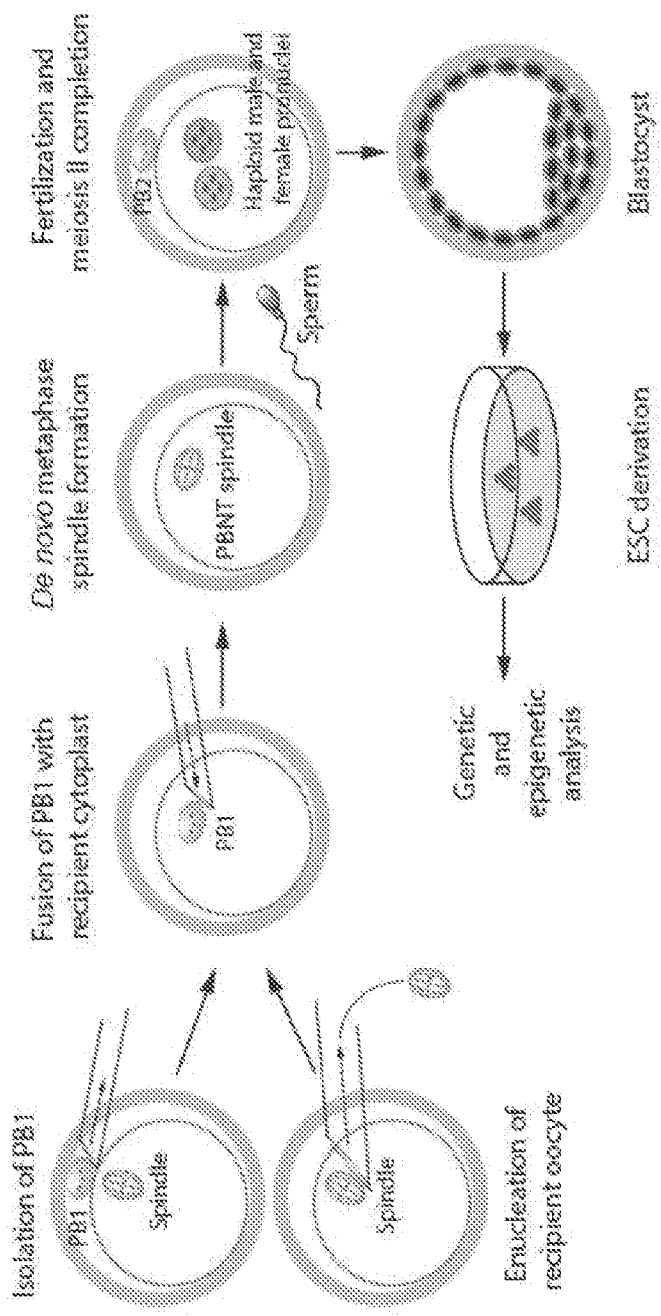
FIG. 1A shows the generation of haploid human oocytes by PBNT. PB1 from a donor oocyte is recovered and introduced into a recipient MII cytoplast. After fertilization, PBNT zygotes are cultured to the blastocyst stage before transfer to a patient. Alternatively, they can be used to derive embryonic stem cells for further analysis.

Interphase nuclei of skin fibroblasts transplanted into enucleated human MII oocytes (cytoplasts) undergo rapid remodeling and cell cycle reprogramming resulting in the formation of oocyte-like MII-arrested spindles (Ma H et al, *Nature* 511, 177-183 (2014); Tachibana M et al, *Cell* 153, 1228-1238 (2013); both of which are incorporated by reference herein). Residual meiotic activity in cytoplasts capable of forming de novo MII spindles is critical for reprogramming and subsequent embryonic development following somatic cell nuclear transfer (SCNT). Since the main purpose of human SCNT is to produce autologous ESCs, MII-arrested SCNT oocytes are not fertilized with sperm but activated artificially to exit meiotic arrest, while segregation of chromosomes during the second meiotic division is suppressed to preserve the diploid somatic cell genome. The reprogramming potential of meiotic oocyte cytoplasm, as demonstrated by SCNT, suggested the possibility of producing haploid oocytes with donor genomes in the context of a treatment for infertility. Previous mouse studies demonstrated that both PB1 and PB2 genomes can be reconstituted by transfer into compatible MII or zygotic cytoplasm and contribute to development of viable offspring (Wakayama T et al, *J Reprod Fertil* 110, 263-266 (1997); Wakayama T and Yanagimachi R, *Biol of Reproduction* 59, 100-104 (1998); incorporated by reference herein). However, these murine studies have not been translated to other species including primates and humans. Disclosed herein is the generation of haploid human oocytes following transfer of PB1 genomes into enucleated MII oocytes and induction of de novo meiosis II after fertilization with sperm (FIG. 1A). Preimplantation development of PBNT oocytes to blastocysts and ESCs was also studied and their genetic and epigenetic properties determined.

Previous mouse studies demonstrated that both polar body genomes retain the potential to participate in normal development or form ESCs if reintroduced into corresponding oocyte or zygotic cytoplasm (Wakayama S et al, *Stem Cells* 25, 986-993 (2007) and Wang T et al, *Cell* 157, 1591-1604 (2014); both of which are incorporated by reference herein). Disclosed herein is the translation of these mouse discoveries and the demonstration that PBNT can rescue the genetic material of developmentally discarded human PB1 genomes. Residual meiotic activity in enucleated MII oocytes is sufficient to induce formation of de novo functional, MII-like spindles that result in haploid oocyte upon fertilization. Using noninvasive birefringence imaging, it was found that most PBNT oocytes (67%) formed visible spindles within 60 min of fusion. However, more detailed spindle morphology analysis in stained oocytes revealed that some meiotic spindles were at prophase or anaphase, suggesting compromised nuclear content in PB1. Furthermore, approximately half of normally fertilized PBNT zygotes arrest before reaching the blastocyst stage, suggesting that efforts to optimize protocols in the timing of oocyte harvest for isolating viable PBs are appropriate.

Aneuploidy in IVF embryos is relatively common (Alfarawati S et al, *Fertil Steril* 95, 520-524 (2011) and Angell R R et al, *Nature* 303, 336-338 (1983); incorporated by reference herein) and, as shown here, also occurs in PBNT blastocysts. Aneuploidy rates in human embryos increase with maternal age as a result of meiosis I or II errors (Hassold T and Hunt P, *Nat Rev Genet* 2, 280-291 (2001); Nagaoka S I et al, *Nat Rev Genet* 13, 493-504 (2012); Petronczki M et al, *Cell* 112, 423-440 (2003); incorporated by reference herein). In addition, mitotic errors during-post zygotic cleavage divisions may occur, producing mosaic blastomeres containing multiple distinct karyotypes within a preimplantation embryo (McCoy R C et al, *PLoS Genetics* 11, e1005601 (2015); incorporated by reference herein). While PBNT is unlikely to correct meiosis I errors, functional cytoplasm from young donors may reduce incidences of aneuploidy resulting from meiosis II or mitotic errors. Aneuploidy rates in normally fertilized PBNT blastocysts in the current study were similar to controls based on STR and Array-CGH analyses. It is likely that that further optimizations of PBNT protocols will reduce aneuploidy rates. Nevertheless, implementing preimplantation genetic screening (PGS) is critical prior to clinical applications of PBNT oocytes.

Due to the current trend toward delayed childbearing in the Western world, age-related infertility with concomitant decreases in ovarian reserve is common (Bellieni C V, *World J Clin Pediatr* 1, 34-36 (2012); incorporated by reference herein). It is disclosed herein that generating additional oocytes by rescuing PB1 would increase the yield of patient-related blastocysts available for transfer from a single stimulation cycle. This implies that utilization of PBNT may significantly improve ART outcomes and pregnancy rates, particularly for women of advanced age with decreased ovarian reserve. However, this therapy is based on availability of patient PB1, and therefore, is not applicable for women who cannot produce mature oocytes (Bilgin E M and Kovanci E, *Curr Opin Obst Gynecol* 27, 167-174 (2015); Grynberg M et al, *Fertil Steril* 105, 13-19 (2016); both of which are incorporated by reference herein). Moreover, PBNT technology will be limited to countries, such as the United States, where IVF programs are allowed to coordinate oocyte donation cycles with compensation of donors. Polar body biopsy is an established technique in IVF and its removal from patient oocytes does not affect fertilization and subsequent embryo development (Cimadomo D et al, *Biomed Res Int* 2016, 7193075 (2016). Since PBNT relies on donor oocytes, this strategy allows complementation of PB genomes from older women with young donor cytoplasts.

Expanded use of PBNT, in addition to spindle transfer (ST), could provide an additional technique to support mitochondrial replacement therapy (MRT); a promising approach to avoid maternal transmission of mtDNA-based disease (Tachibana M et al, *Nature* 493, 627-631 (2013) and Tachibana M et al, *Nature* 461, 367-372 (2009); both of which are incorporated by reference herein). In mice, it has been demonstrated that a minimal mtDNA carryover can be achieved in offspring generated by polar body transfer (Wang T et al, *Cell* 157, 1591-1604 (2014) and Yamada M et al, *Cell Stem Cell* 18, 749-754 (2016); both of which are incorporated by reference herein). Disclosed herein is data suggesting that in conjunction with ST, PBNT could potentially increase the number of reconstructed MRT oocytes for families with mtDNA-based defects. Similar to other MRT technologies, PBNT will have to meet safety and efficacy requirements of regulatory agencies before approval for routine clinical applications (Wolf D P et al, *Trends Mol Med* 21, 68-76 (2015); incorporated by reference herein). In addition, PBNT provides a tool to study basic mechanisms of developmental biology related to female meiosis and expands the understanding of the genetic stability in oocytes.

EXAMPLES

The following examples are for illustration only. In light of this disclosure, those of skill in the art will recognize that variations of these examples and other examples of the disclosed invention be possible without undue experimentation.

Example 1

De Novo Formation of MII Spindles from the PB1 Genomes

It was first determined whether the residual meiotic activity in enucleated human MII oocytes is sufficient to induce formation of morphologically normal MII-like spindles from the PB1 genome, carrying a genetic complement of MII chromosomes (Hou Y et al, *Cell* 155, 1492-1506 (2013); incorporated by reference herein). To this end, fresh MII oocytes donated by and retrieved from 11 healthy volunteers (25-31 years) were used following controlled ovarian stimulation (COS) protocols and transvaginal follicular aspirations.

Figure 1B:
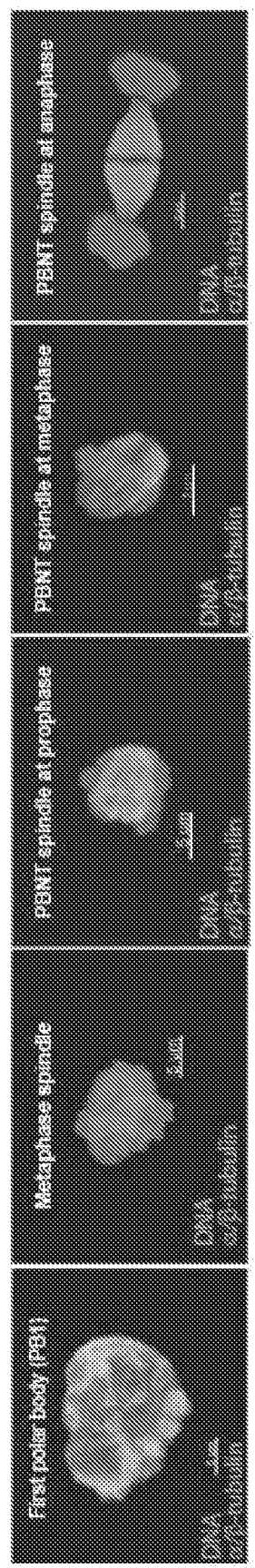
FIG. 1B shows confocal microscopy detecting meiotic spindle-chromosomal structures in PB1 (first panel from left), intact MII (second panel) and PBNT (third-last panels) oocytes labelled with DAPI (blue) for DNA and α- and β-tubulins (green) for microtubules. Note absence of meiotic spindle apparatus in PB1 (first panel) and abnormal spindles at prophase (third panel) or anaphase (last panel) in some PBNT oocytes. Scale bars, 5 μm.
Figure 1C:
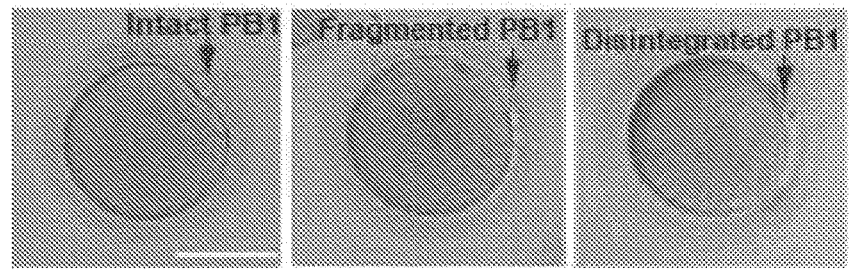
FIG. 1C shows most PB1s in freshly retrieved human MII oocytes were intact with round morphology (left panel). Other MII oocytes contained fragmented or disintegrated PB1s, unsuitable for PBNT (middle and right panels). Scale bar, 100 μm.
Figure 1D:
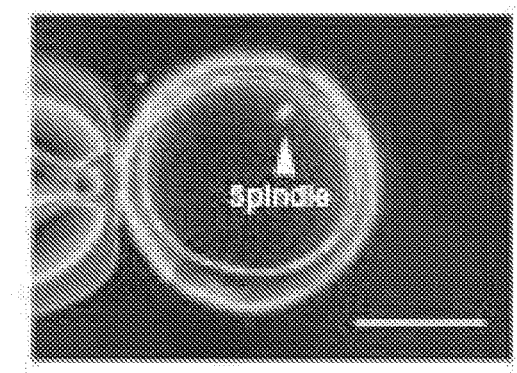
FIG. 1D shows spindle formation (arrow), detected using the Oosight™ imaging system, 60 min after PB1 was introduced into an enucleated MII cytoplast. Scale bar, 100 μm.

Using immunochemistry with antibodies against α and β tubulins and 4',6-diamidino-2-phenylindole (DAPI) for DNA staining, it was determined that intact PB1s in mature, human MII oocytes do not contain detectable metaphase spindles, possibly due to a rapid decline in meiotic factors after abstriction (FIG. 1B). Reconstructed PBNT oocytes were produced by fusing intact, round PB1 with MII cytoplasts (FIGS. 1A and 1C). Noninvasive imaging indicated that most PBNT oocytes (67%) formed visible spindles within 60 min of fusion (FIG. 1D). Labeling with antibodies for α and β tubulins and DAPI demonstrated that all PBNT oocytes (n=5) contained spindle-chromosomal complexes. However, only 2 experimental oocytes formed metaphase spindles similar to intact MII oocytes. The remaining PBNT spindles were at prophase (n=2) or anaphase (n=1) (FIG. 1B) likely reflecting compromised nuclear content.

Example 2

Figure 1E:
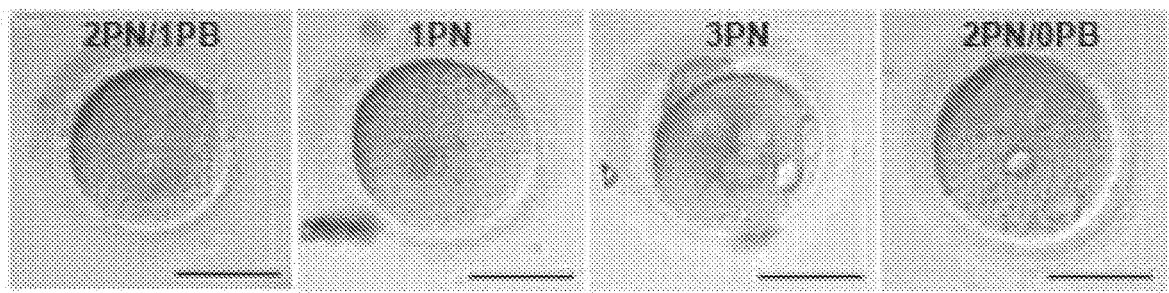
FIG. 1E shows the completion of meiosis and pronuclear formation in human PBNT oocytes after fertilization. Note normal zygote with 2 pronuclei (2PN) and a second polar body (PB2) on left panel and abnormal 1PN, 3PN or 2PN without PB2 extrusion in other images. Scale bars, 100 μm.

Resumption and Completion of Meiosis II in PBNT Oocytes following Fertilization with Sperm When the functionality of meiotic spindles in reconstructed PBNT oocytes was examined post-fertilization, by intracytoplasmic sperm injection (ICSI), completion of meiosis II was evidenced by the abstriction of PB2 and formation of pronuclei. Most PBNT oocytes survived ICSI (97%; 31/32) and formed visible pronuclei (81%; 25/31) at rates similar to non-manipulated intact controls (Table 1). The majority of fertilized PBNT zygotes (76%; 19/25) contained 2 pronuclei (PN) and a second polar body (PB2) indicative of normal meiosis II completion (FIG. 1E). The remaining zygotes carried irregular numbers of pronuclei (1 or 3) or failed to extrude PB2 (FIG. 1E; Table 1). These outcomes were slightly lower than the control (Table 1) indicative that the majority of PBNT oocytes form functional spindles capable of recapitulating meiosis II after fertilization.

TABLE 1

Completion of Meiosis II in PBNT and Intact, Control MII Oocytes after Fertilization

| Group | No. of oocytes | Survival after ICSI (%) | Fertilization rate (%) | Normal meiosis II completion (%) | Abnormal meiosis II completion | | |
|---|---|---|---|---|---|---|---|
| | | | | | 3 PN (%) | 1PN (%) | 2PN/0PB (%) |
| PBNT | 32 | 31/32, (97 ± 1) | 25/31, (81 ± 8) | 19/25, (76 ± 10) | 2/25, (8 ± 10) | 2/25, (8 ± 5) | 2/25, (8 ± 7) |
| Control | 21 | 20/21, (95 ± 6) | 17/20, (85 ± 8) | 16/17, (94 ± 4) | 0/17, (0) | 1/17, (6 ± 4) | 0/17, (0) |

Example 3

Preimplantation Development and Ploidy of PBNT Blastocysts

Figure 1F:
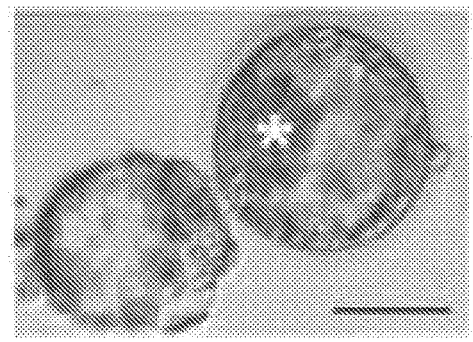
FIG. 1F shows a hatching blastocyst from a PBNT zygote, with prominent ICM indicated by asterisk. Scale bar, 100 μm.
Figure 1G:
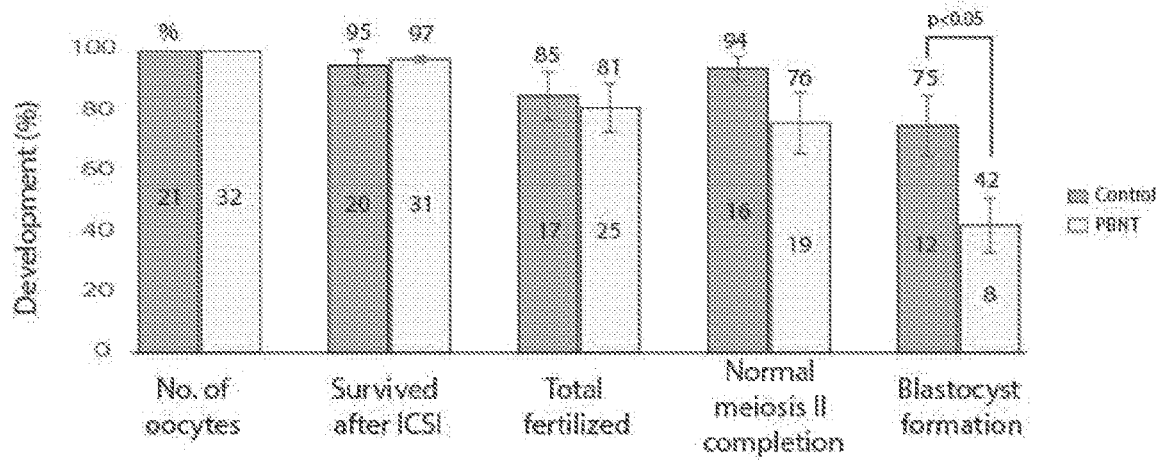
FIG. 1G shows a summary of fertilization and in vitro development to blastocysts of PBNT oocytes. Error bars are mean±SEM. Significance established with Student's t-test. Control=intact MII oocytes.
Figure 2A:
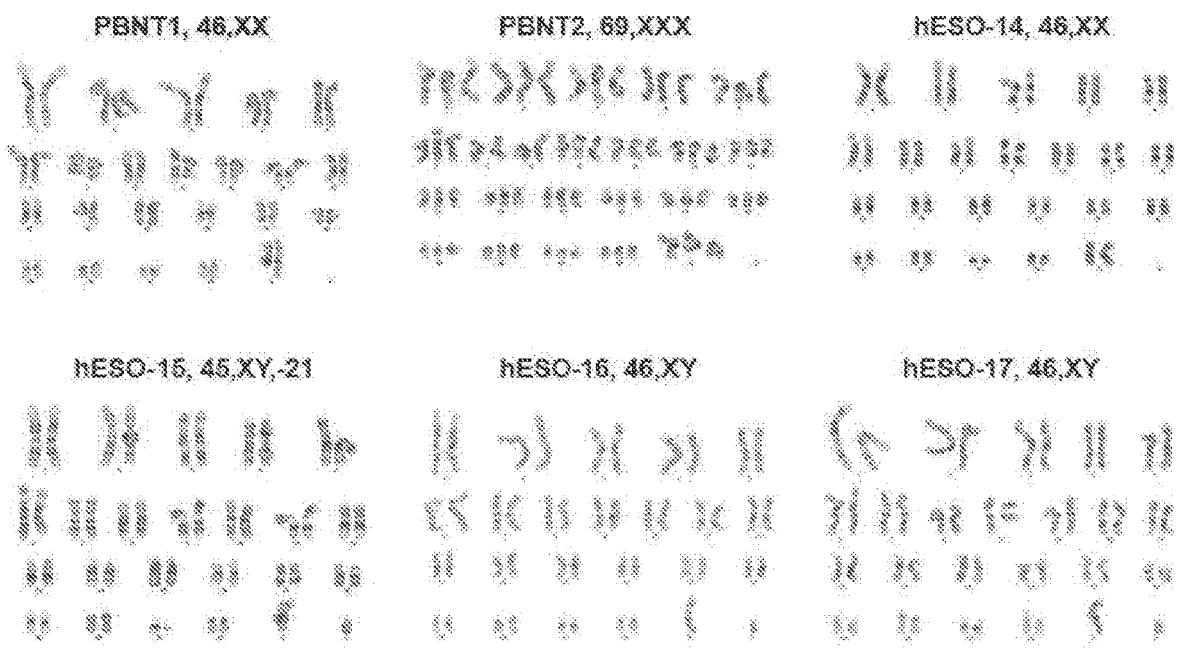
FIG. 2A shows cytogenetic G-banding analysis of PBNT1, PBNT2, and control hESO-14, hESO-15, hESO-16 and hESO-17 lines. Note, the normal female karyotypes in PBNT1 and control hESO-14 and normal male karyotypes in control hESO-16 and hESO-17. PBNT2 displayed an abnormal triploid karyotype while control hESO-15 had an abnormal karyotype with chromosome 21 monosomy.

To examine developmental competency, normally fertilized PBNT zygotes and controls were cultured to the blastocyst stage. Similar to controls, 95% (18/19) of PBNT zygotes cleaved, 74% (14/19) reached 8-cell and 68% (13/19) formed compact morula stage embryos (Table 2). In the control group, 75% (12/16) of the zygotes reached blastocysts while only 42% (8/19) of PBNT zygotes did (Student's t-test, p<0.05, FIG. 1F, 1G and Table 2). Since embryonic aneuploidy resulting from numerical chromosomal abnormalities leading to implantation failure or spontaneous pregnancy loss is common irrespective of blastocyst morphology, selected PBNT (n=2) and control (n=3) blastocysts were subjected to short tandem repeat (STR) analysis. Examination of microsatellite markers mapping to 22 human autosomal loci and one X-linked locus revealed that two sampled PBNT blastocysts contained normal diploid chromosomes contributed from both oocyte and sperm. These results minimized the possibility of errors in oocyte meiotic chromosomal segregation. Three additional PBNT blastocysts were subjected to trophectoderm biopsy and performed array comparative genomic hybridization (Array-CGH) analysis and determined that two were normal but one blastocyst was aneuploid (loss of 17). This outcome was comparable to controls with one aneuploid blastocyst out of three tested (loss of 21).

derived from five PBNT blastocysts. The line was designated PBNT1 (FIG. 1F). An additional four ESC lines were developed from nine control blastocysts. This included hESO-14, which was a genetically related sibling of PBNT1, derived from the same egg and sperm donors. Lower ESC derivation efficiency (20%, 1/5) from PBNT embryos compared to controls (44%, 4/9) may indicate poor quality of PBNT blastocysts but total numbers were low for definitive conclusions. One ESC line (PBNT2) was derived from two blastocysts grown from abnormal (3PN) PBNT zygotes. Cytogenetic G-banding revealed that PBNT1 and three of the four control ESCs exhibited normal diploid karyotypes with no evidence of detectable numerical or structural chromosomal abnormalities (FIG. 2A). The remaining control hESO-15 was aneuploid with chromosome 21 monosomy (FIG. 2A). In addition, STR analysis of PBNT1 and hESO-14 confirmed their normal ploidy and sibling relationship (Table 3). As expected, PBNT2 displayed a 66-69, XXX triploid karyotype (FIG. 2A). DNA fingerprinting by STR corroborated the presence of three alleles for chromosomes 2, 6, 13, 18, and 22 and four alleles on chromosome 12 in this cell line (Table 3). On the basis of allelic inheritance analysis, the triploid karyotype was caused by failed meiosis II completion with retention of PB2 genetic material. This was consistent with observation of 3 pronuclei

TABLE 2

Preimplantation Development of PBNT and Control Zygotes

| Group | No. of oocytes with normal meiosis II completion | 2 cell (%) | 8 cell (%) | Compact morula (%) | Blastocyst (%) |
|---|---|---|---|---|---|
| PBNT | 19 | 18/19, (95 ± 2) | 14/19, (74 ± 17) | 13/19, (68 ± 18) | 8/19, (42 ± 9)$^a$ |
| Control | 16 | 16/16, (100) | 15/16, (96 ± 4) | 14/16, (88 ± 5) | 12/16, (75 ± 10)$^b$ |

$^{a,b}$Different superscripts within a column indicate significant differences (P < 0.05).

Example 4

Genetic Integrity in ESCs Derived from PBNT Embryos

Figure 5A:
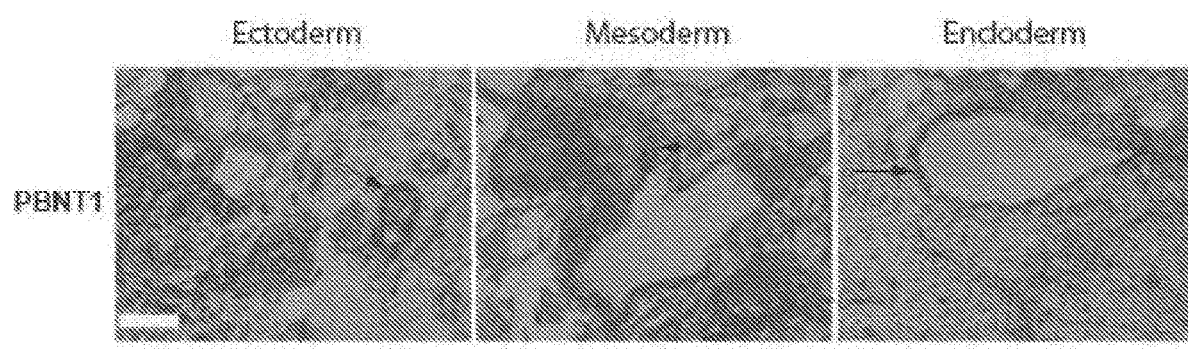
FIG. 5A shows histological analyses of teratoma tumors produced after injections of PBNT1 into SCID mice. Scale bars, 100 μm. Arrows indicate neural crest-like tissues (ectoderm), cartilage-like tissues (mesoderm) and mucosal epithelium of gut-like tissues (endoderm).
Figure 5B:
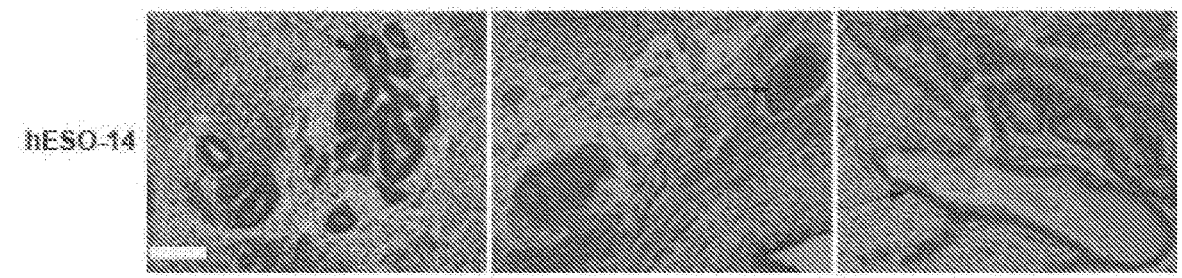
FIG. 5B shows histological analyses of teratoma tumors produced after injections of hESO-14 into SCID mice. Scale bars, 100 μm. Arrows indicate neural crest-like tissues (ectoderm), cartilage-like tissues (mesoderm) and mucosal epithelium of gut-like tissues (endoderm).

In an effort to further define the potential clinical utility of reconstructed, haploid PBNT oocytes, one ESC line was and failure to segregate a second polar body after fertilization in these zygotes. In addition, the sperm also contributed a second allele to chromosome 12 tetraploidy. Both PBNT1 and control hESO-14 lines maintained typical ESC morphology and formed teratoma tumors containing cells and tissues from all three germ layers (FIGS. 5A and 6B).

TABLE 3

Parentage Analysis of PBNT1, PBNT2, and hESO-14 Determined by Short Tandem Repeat (STR) Assay

| STR loci | PBNT1 | hESO-14 | Oocyte donor1 | Sperm donor1 | PBNT2 | Oocyte donor2 | Sperm donor2 |
|---|---|---|---|---|---|---|---|
| Sex | F | F | F | M | F | F | M |
| AME | XX | XX | XX | XY | XXX | XX | XY |
| D1S548 | 152/176 | 152/176 | 152/168 | 168/176 | 168/172 | 152/168 | 152/172 |
| D2S1333 | 297/301 | 289/317 | 297/317 | 289/301 | 285/301/305 | 285/301 | 305/305 |
| D3S1768 | 192/200 | 192/200 | 200/200 | 192/192 | 188/196 | 188/196 | 196/200 |
| D4S2365 | 296/300 | 296/296 | 296/300 | 296/296 | 296/300 | 296/300 | 296/296 |
| D4S413 | 123/161 | 123/125 | 125/161 | 123/123 | 123/125 | 123/123 | 123/125 |
| D5S1457 | 123/123 | 101/105 | 101/123 | 105/123 | 119/123 | 123/123 | 119/123 |
| D6S276 | 227/249 | 227/249 | 249/251 | 227/235 | 227/235/237 | 227/235 | 237/251 |
| D6S501 | 164/172 | 164/172 | 172/172 | 164/168 | 164/168/172 | 168/172 | 164/172 |
| D11S2002 | 254/254 | 254/254 | 254/254 | 254/254 | 254/254 | 254/254 | 254/254 |
| D11S925 | 299/300 | 297/300 | 282/300 | 297/299 | 282/305 | 305/305 | 282/282 |

TABLE 3-continued

Parentage Analysis of PBNT1, PBNT2, and hESO-14
Determined by Short Tandem Repeat (STR) Assay

| STR loci | PBNT1 | hESO-14 | Oocyte donor1 | Sperm donor1 | PBNT2 | Oocyte donor2 | Sperm donor2 |
|---|---|---|---|---|---|---|---|
| D12S364 | 264/286 | 264/286 | 276/286 | 264/274 | 270/272/274 | 270/272 | 270/274 |
| D12S67 | 248/260 | 248/260 | 252/260 | 248/264 | 252/256/260/264 | 252/260 | 256/264 |
| D13S765 | 188/200 | 188/196 | 188/192 | 196/200 | 188/192/200 | 188/200 | 188/192 |
| D16S403 | 143/145 | 137/145 | 145/145 | 137/143 | 135/145 | 145/145 | 135/149 |
| D17S1300 | 261/265 | 261/265 | 265/265 | 249/261 | 265/269 | 257/269 | 257/265 |
| D18S537 | 204/204 | 204/204 | 200/204 | 204/204 | 196/200/208 | 196/208 | 200/204 |
| D18S72 | 301/305 | 301/307 | 301/305 | 305/307 | 301/305 | 301/305 | 301/305 |
| D22S685 | 184/188 | 184/188 | 188/188 | 184/188 | 180/192/196 | 180/192 | 192/196 |
| DXS2506 | 278/282 | 278/282 | 282/282 | 278* | 183/183 | 183/199 | 183* |
| MFGT22 | 104/108 | 104/104 | 104/108 | 104/108 | 108/108 | 108/112 | 108/108 |

*Only male samples show one mark of DXS2506 on X chromosome.

Figure 2B:
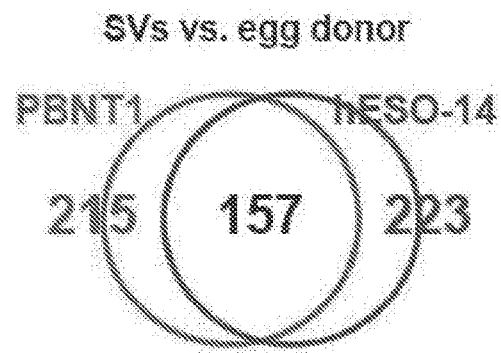
FIG. 2B shows a Venn diagram displaying the results of structural variation analysis in PBNT1, hESO-14 compared to the egg donor. PBNT1 (blue) and hESO-14 (red) had similar numbers of SVs when compared to the egg donor.
Figure 2C:
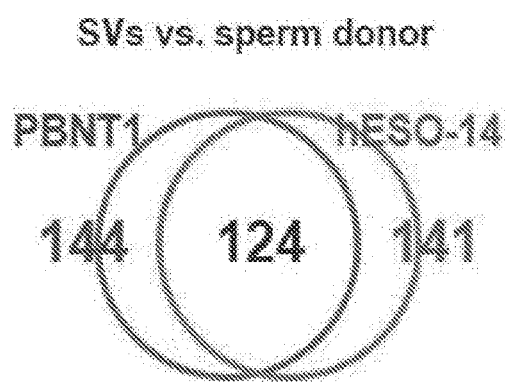
FIG. 2C shows a Venn diagram displaying the results of structural variation analysis in PBNT1, hESO-14 compared to the sperm donor. PBNT1 (blue) and hESO-14 (red) had similar numbers of SVs when compared to the sperm donor.
Figure 2D:
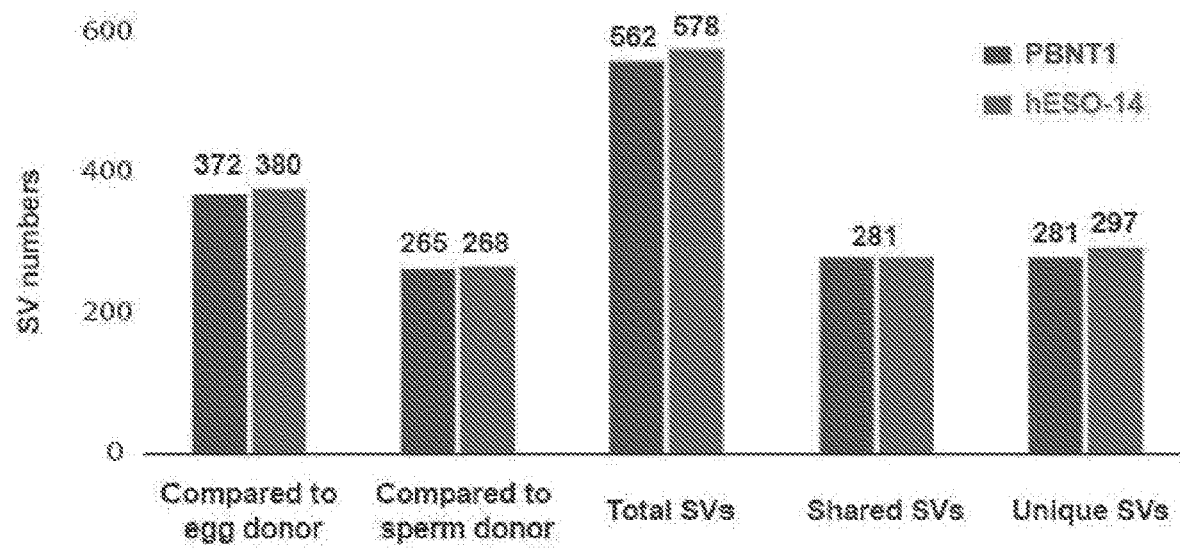
FIG. 2D shows a summary of SVs in PBNT1 and hESO-14.

To evaluate if PBNT introduced subchromosomal changes undetectable by G-banding, genome-wide, high-resolution genome physical maps of PBNT1 and hESO-14 lines, as well as the egg and sperm donor DNA were generated. The BioNano Genomics Irys platform (Mak A C et al, *Cell Stem Cell* 5, 11-14 (2016); incorporated by reference herein) enables detection of structural variations (SVs) including insertions, deletions and inversions at 1-kb resolution. When compared to the egg donor genome, 372 SVs were identified in PBNT1 and 380 SVs in hESO-14, of which 157 were shared between these sibling cell lines (FIG. 2B). Compared to the sperm donor genome, 268 SVs were detected in PBNT1 and 265 SVs in hESO-14 with 124 common SVs (FIG. 2C). In addition, comparable numbers of unique SVs were identified in PBNT1 (281) and hESO-14 (297) (FIG. 2D). No genes were found within or close to SVs that were differentially expressed between PBNT1 and hESO-14.

Example 5

Epigenetic and Transcriptional Signatures of PBNT ESCs

Figure 3A:
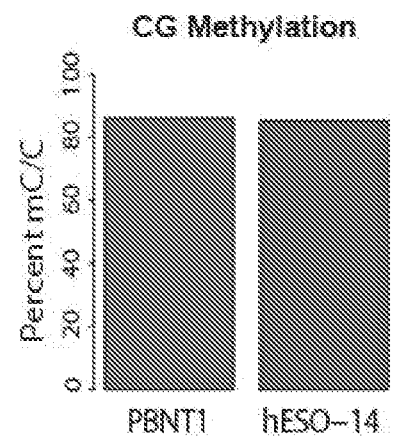
FIG. 3A shows the percentage of methylated CGs in PBNT1 and hESO-14 from total CG sites.
Figure 3B:
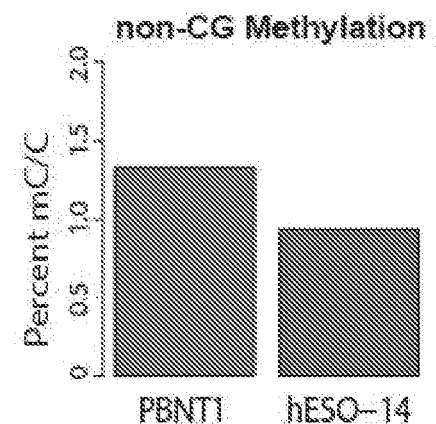
FIG. 3B shows non-CG methylation rates in PBNT1 and hESO-14 among all non-CG sites.
Figure 3C:
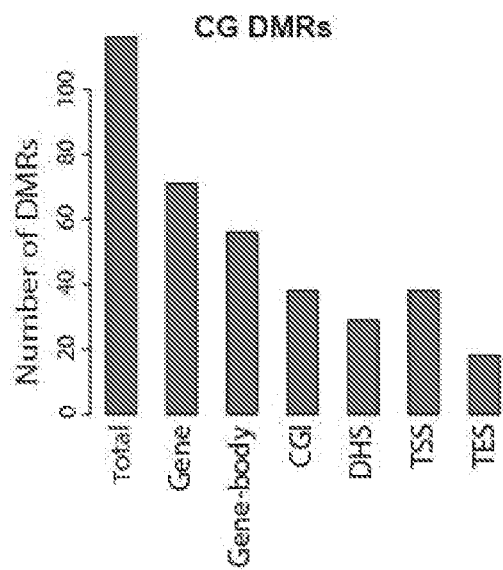
FIG. 3C shows a total of 116 CG DMRs were identified between PBNT1 and hESO-14. Genomic features of DMRs (overlap at least 1 bp)—CGI, CG islands; DHS, DNase I hypersensitivity sites, TSS, transcription start sites; TES, transcription end sites.
Figure 3D:
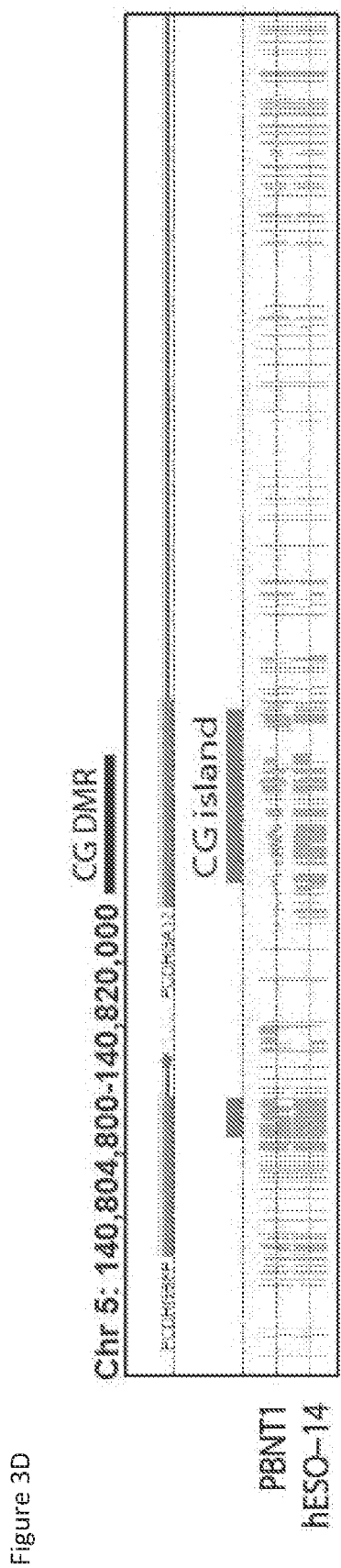
FIG. 3D shows a representative screen shot showing one CG DMR hypomethylated in PBNT1 compared to hESO-14.
Figure 3E:
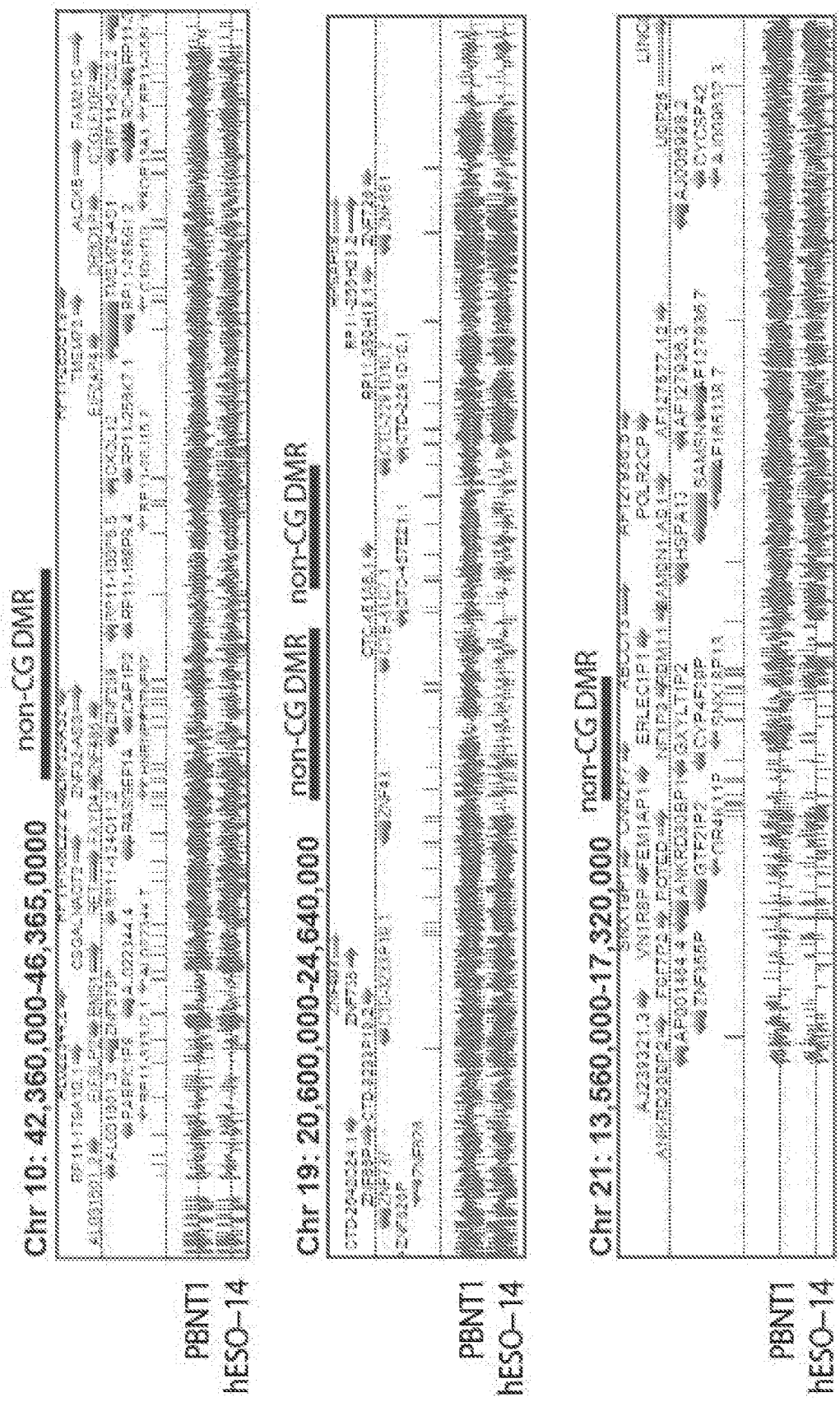
FIG. 3E is a set of screen shots showing four non-CG mega DMRs identified in PBNT1 compared to hESO-14.

DNA methylation involving the covalent transfer of a methyl group to the fifth carbon atom of the cytosine ring is an important epigenetic mechanism defining cell identity (Smith Z D and Meissner A, *Nat Rev Genet* 14, 204-220 (2013); incorporated by reference herein). This process undergoes dynamic changes during and after fertilization reflecting developmental reprogramming (Canovas S and Ross P J, *Theriogenology* 86, 69-79 (2016); incorporated by reference herein). Also, the establishment of stable ESCs is associated with major changes in methylation profiles as the genome reconfigures to the pluripotent state (Lister R et al, *Nature* 462, 315-322 (2009); Lister R et al, *Nature* 471, 68-73 (2011); both of which are incorporated by reference herein). To evaluate the normalcy of these changes, genome-wide DNA methylation analyses of PBNT1 and hESO-14 cell lines were conducted using high-coverage, base-resolution MethylC-seq (Lister 2009 supra). Both lines showed similar levels of CG methylation, a difference of only 0.7% between PBNT1 (86.1%) and hESO-14 (85.4%), and non-CG methylation, a difference of only 0.4% between PBNT1 (1.3%) and hESO-14 (0.9%) (FIGS. 3A and 3B). Pairwise comparison of these two samples identified only 116 CG differentially methylated regions (DMRs) and 4 non-CG mega DMRs spanning about 500 kb (He Y and Ecker J R, *Ann Rev Genom Hum Genet* 16, 55-77 (2015); incorporated by reference herein) (FIG. 3C; Table S5, FDR<0.01). Visual inspection implied the conformation of these DMRs (FIGS. 3D and 3E), but there was no enrichment in gene ontology (GO) terms, genetic features (FIG. 3C), or correlation to the transcriptional profile. These outcomes suggest that the global methylation profile of experimental PBNT1 appeared very similar to control hESO-14.

Figure 4A:
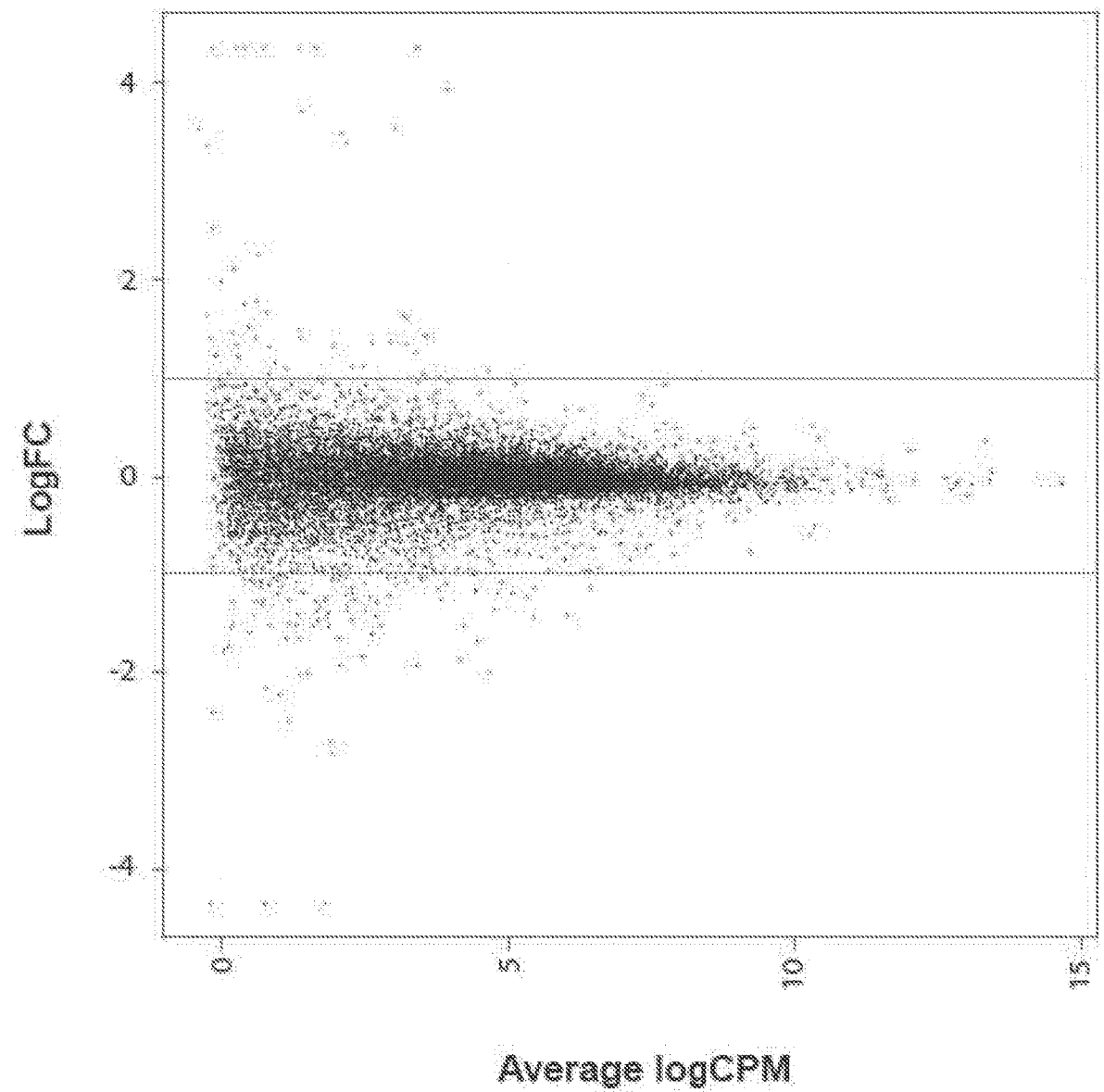
FIG. 4A is a smear plot summarizes the differential expression (DE) analysis. The log-fold change of each of the 14877 genes used in the analysis is plotted against the average abundance (log of counts-per-million) of each gene. The red dots represent the genes with significantly different expression (FDR<0.05). The blue lines indicate 2-fold changes.
Figure 4B:
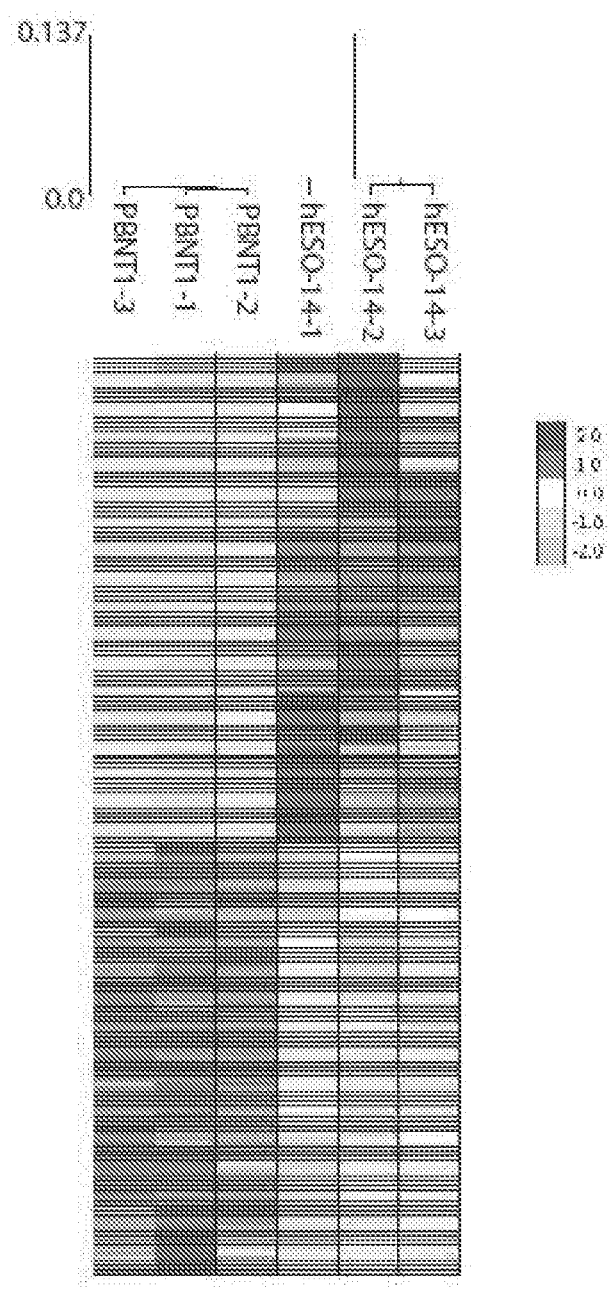
FIG. 4B is a heat map showing the expression profile of the 186 DE genes. Two distinct clusters were apparent with genes expressed highly in PBNT1 cells compared to hESO-14 cells and vice versa (n=6).

Finally, global gene expression patterns were examined in the PBNT1 and hESO-14 lines. Deep sequencing (50M reads) by RNA-seq was performed in triplicates for each of the two lines. Differential expression analysis was performed using the edgeR package (Robinson M D and Smyth G K, *Biostatistics* 9, 321-332 (2008); incorporated by reference herein) and showed that only 1.25% of the examined genes (186 out of 14,876) were differentially expressed between PBNT1 and hESO-14 (FIGS. 4A and 4B, FDR<0.05). Using Gene Ontology (GO) analysis, various GO terms were allocated. However, no statistically enriched functional categories for the differentially expressed genes were identified. These data indicated that the global gene expression patterns of PBNT1 cells closely resembled those of control hESO-14 cells.

Thus, within the limits of these analyses, the PB1 genome interacts with oocyte cytoplasm establishing epigenetic and transcriptome characteristics that emulate the pluripotent state.

Example 6

Gamete Donation

Oocyte donors 25-31 years of age were recruited through the OHSU Women's Health Research Unit. Two healthy sperm donors were also recruited. Eligible participants attended an information session describing study goals and related procedures. Written informed consent was obtained from all gamete donors stating that oocytes will be fertilized to create embryos for research purposes and will not be used for reproductive purposes but rather will be studied in vitro including generation of embryonic stem cells.

Example 7

Methods

To produce recipient MII cytoplasts, oocytes were placed into a 50 µl manipulation droplet of human tubal fluid with HEPES 10% medium containing 5 µg/ml cytochalasin B (HTF w/HEPES 10% CB) in a glass bottom dish. The droplet was covered with tissue culture oil and oocytes were maintained at 37° C. for 10 min before enucleation. The dish was mounted on the stage of an inverted microscope (Olympus IX71) equipped with a stage warmer (http://www.tokai-hit.com), Narishige micromanipulators, Oosight Imaging System (http://wwwcri-inc.com), and laser objective (http://www.hamiltonthome.com) (websites and contents incorporated by reference herein). An oocyte was positioned using a holding pipette so that the spindle was situated at a position of about 2-4 o'clock. The zona pellucida next to the spindle was laser drilled and then an enucleation pipette was introduced through the slit. The spindle was extracted by aspiration into the pipette with a minimal amount of cytoplasm and surrounding plasma membrane and discarded.

For polar body isolation, an oocyte was positioned with the first polar body (PB1) at 2 o'clock, and the zona pellucida was drilled before a transfer pipette was introduced and the PB1 aspirated. The PB1 was then transferred briefly into a drop containing HVJ-E extract (Ishihara Sangyo Kaisha) diluted 1:3 with HTF w/HEPES 10% CB, transferred and rinsed in HTF w/HEPES 10% CB, and placed in the perivitelline space of the recipient cytoplast. The couplets were rinsed in HTF w/HEPES 10%, transferred to Global 10% medium, and incubated at 37° C. in 6% $CO_2$ for 60 min to allow fusion. Fusion was confirmed 30-60 min after nuclear transfer and PBNT oocytes were fertilized after an additional 50 min culture using intracytoplasmic sperm injection (ICSI) using fresh donor sperm. Fertilized oocytes were then cultured in Global 10% medium at 37° C. in 6% $CO_2$, 5% $O_2$ and 89% $N_2$. Fertilization was determined 16 hours after ICSI by noting pronuclear formation and polar body extrusion. Non-manipulated intact MiI oocytes served as controls that were fertilized and cultured similar to the PBNT group.

The following examples also help demonstrate examples within the present scope in regard to oocytes prepared to overcome problems with poor mitochondrial genomics.

Example 8

Inclusion and Exclusion Criteria

Since mitochondrial disease can be attributed to genome mutations in mtDNA and/or nuclear DNA (Wallace D C, *J Clin Invest* 123, 1405-1412 (2013); incorporated by reference herein), an important clinical challenge is to confirm pathogenic mtDNA mutations in families eligible for MRT. Five families—four diagnosed with Leigh syndrome (LS) and one with MELAS—were recruited and genetic testing performed to confirm maternally inherited mtDNA mutations. DNA was collected from blood, skin fibroblasts (SF) and/or urine from children and mothers, and whole mtDNA sequencing was performed. The first LS family had an affected 2-year-old child with a homoplasmic T8993G substitution in both blood and SF samples while her 22-year-old mother had the same mutation with 70% heteroplasmy in blood and 100% in SF (FIG. 6A, left).

In the second related LS family, an affected 2.5-year old child carried the same T8993G mutation at 95% heteroplasmy in blood and 100% in SF while in a second 1-year old asymptomatic sibling, the mutation load was 50% in blood and 62% in SF. Their 23-year-old mother, who was the elder sister of the subject from the first family, carried this mutation at 13% in blood and 16% in SF (FIG. 6A, right).

In the third LS family, the affected 12-year-old boy harbored a G13513A substitution at 56%, 86% and 97% heteroplasmy in blood, SF and urine, respectively. His asymptomatic 19-year-old brother carried same mutation at 10%, 14% and 23% heteroplasmy levels in blood, SF and urine, respectively. Their 36-year-old mother also harbored the mutation at 3%, 98% and 39% levels in blood, SF and urine, respectively (FIG. 6B).

A fourth family also presented with a 1-year-old child diagnosed with LS. However, genetic screening did not reveal any pathogenic mtDNA mutations in the child or mother.

The fifth family was from a large, well-studied MELAS pedigree carrying a pathogenic A3243G mutation (FIG. 10B) (McClelland K, 2014, https://scholarworks.csustan.edu/bitstream/handle/011235813/793/McClellandK.summer201 4%20.pdf?sequence=1; website last accessed 28 Nov. 2016 and incorporated by reference herein). The 32-year-old mother carried the mutation at 14%, 47% and 35% in blood, SF and urine, respectively. All her 3 children inherited this mutation (FIG. 6C).

These results indicated that maternally transmitted, pathogenic mtDNA mutations were implicated in four of the five families studied. The clinical LS phenotype in the fourth family was not associated with any pathogenic mtDNA mutation and thus was excluded from further analyses. This highlights the importance of genetic testing for maternally inherited mtDNA diseases prior to MRT. Moreover, since heteroplasmy levels may vary among different tissues, it is critical to sample and test blood, skin and urine, in both mothers and children (Monnot S et al, *Hum Mutat* 32, 116-125 (2011); incorporated by reference herein).

Healthy volunteer oocyte donors were also screened and it was confirmed that they did not carry any inherited pathogenic mtDNA mutations. Their mtDNA sequences and corresponding haplotype were subsequently used for matched MRT combinations.

Example 9

COS (Controlled Ovarian Stimulation), Oocyte Recovery and Mutations in Oocytes

Women with mtDNA disease display live birth rates comparable to the general population, therefore, it is accepted that they have normal fertility. However, ovarian response to gonadotropin stimulation and oocyte recovery in women carrying pathogenic mtDNA mutations (carriers) was assessed.

Age was similar between carrier and healthy donors. AMH levels, a measure of ovarian reserve, were lower in carriers than in healthy donors (1.1 vs. 4.8 ng/ml). Antral follicle count (AFC) was also lower in carriers compared to the healthy donors (10.3 vs. 22.3). In addition, the duration of COS was about one day longer in the carriers and their peak blood estradiol (E2) level prior to hCG administration also trended lower. Finally, the total number and the number of mature MII oocytes retrieved were also significantly lower in carriers (5.8 vs. 16.6 and 3.8 vs. 13.2, respectively) (FIGS. 11A, 11B, 11C, 11D, 11E, 11F, and 11G). Of note, one carrier (cED2) exhibited premature luteinization, as evidenced by increased progesterone levels prior to the LH surge (FIG. 11H). Therefore, mutation analyses were performed only on retrieved atretic oocytes.

Although the numbers in the cohort were low (Smeets H J et al, *Ann NY Acad Sci* 1350, 29-36 (2015); incorporated by reference herein), the results suggest that mtDNA mutation could lead to reduced ovarian response. Older age and higher BMI in carriers could also have affected the outcome (Kelsey T W et al, *PLoS One* 6, e22024 (2011) and Kelsey T W et al, *Mol Hum Reprod* 18, 79-87 (2012); both of which are incorporated by reference herein). Another potential contributing factor is the long-term hormonal contraception these women were on prior to ovarian stimulation.

MtDNA mutations were then identified in individual oocytes from the carriers. After MII spindle (nuclear genome) removal, the cytoplasts (mtDNA) were used for sequencing. In the first carrier, two recovered oocytes carried the T8993G mutation at 86% and 96% levels. In the second sibling carrier, heteroplasmy levels in 5 atretic oocytes ranged from 72% to 100%. In 4 oocytes from the third LS carrier, the G13513A mutation levels in 3 eggs were very low (0.6-3%) while the fourth was at 40%. Finally, in nine oocytes from the A3243G MELAS carrier, the mutation was not detected in one egg while the remaining carried 9-52% (FIG. 7A). In seeking a method to predict mutation levels of oocytes, mean heteroplasmy levels in the blood of sibling children highly correlated with oocyte levels (Brown D T et al, Am J Hum Genet 68, 533-536 (2001); incorporated by reference herein) ($R^2$=0.52 vs. 0.85, FIG. 7B).

Next, whole mtDNA sequences were analyzed in carrier oocytes in an effort to screen for secondary mtDNA mutations. Comparisons were made to oocytes from healthy donors. Carrier oocytes contained secondary heteroplasmic mtDNA variants, however the average number per oocyte was not significantly different from healthy controls (2.2 vs. 1.3; p>0.05) (FIG. 7C). Some of these variants were present in several oocytes from the same carrier and were also found in the carrier's blood, skin or in sibling children suggesting recurring germline mutations. However, these variants were non-coding D-loop mutations. Others were found only in one oocyte within the group indicative of de novo mutations (45%). The majority (83%) of these secondary variants were low level heteroplasmic (<15%) mutations (FIG. 11I). MtDNA copy number per oocyte was used as an indirect measure of oocyte quality (Monnot S et al, Hum Mol Genet 22, 1867-1872 (2013) and Fragouli E et al, PLoS Genet 11, e1005241 (2015); both of which are incorporated by reference herein). No significant differences between healthy and carrier oocytes (mean 348,954 vs. 283,605, respectively) were observed (FIG. 7D). A low mtDNA copy number may play a role in diminished ovarian reserve (Boucret L et al, Hum Reprod 30, 1653-1664 (2015); incorporated by reference herein) but no correlation between oocyte copy number and AMH levels was observed herein. (FIG. 11J).

In conclusion, carrier oocytes were of normal quality and the mutations levels in blood of sibling children seem to be of predictive value for mutation in oocyte cohorts.

Example 10

Spindle Transfer (ST) in mtDNA Mutation Carrier Oocytes

Meiotic spindles (karyoplasts; with carryover maternal mtDNA) recovered from carrier MII oocytes (n=13) were transferred to enucleated donor oocytes (cytoplasts; donor mtDNA) (FIG. 8A) while controls involved ST between healthy oocytes (n=36) with preselected mtDNA haplotypes (FIG. 12A). All karyoplasts and cytoplasts survived micromanipulations and fusion except for one in the control group. ST oocytes along with intact (non-manipulated) controls were then fertilized by intracytoplasmic sperm injection (ICSI) and cultured to blastocysts. High fertilization rates, comparable to intact controls, were observed in both ST groups (FIG. 8A and FIGS. 12B and 12C). Subsequent development of diploid carrier ST zygotes to the blastocyst stage was 75%, similar to controls. A similar developmental pattern was observed among carrier ST individuals with different mutation types (8993ST, 13513ST and 3243ST) (FIG. 8B).

To address COS asynchrony, ideally both carriers and healthy donors would undergo same-day retrievals with the end point of a similar number of mature oocytes for ST. An alternative approach to achieve these objectives involves oocyte freezing, storage and thawing. ST between fresh and vitrified oocytes (frozen ST) was conducted. The overall fertilization rate using vitrified oocytes was comparable to fresh ST, while formation of normal diploid zygotes was lower (FIG. 8A). No differences in fertilization were noted between karyoplast versus cytoplast vitrification (FIG. 12D).

Since risk of miscommunication between nuclear and mitochondrial genomes has led to concerns regarding the potential secondary metabolic dysfunction (Woodson J D & Chory J, Nat Rev Genet 9, 383-395 (2008); incorporated by reference herein), ST embryo development was analyzed as a function of donor mtDNA sequence distance. ST oocytes and embryos were grouped based on the number of single nucleotide polymorphisms (SNPs) between the original (maternal) and donor oocyte mtDNA, ranging from the close (6 SNPs) to middle (33 SNPs) and to distant (57 SNPs) (FIG. 12A). Fertilization and blastulation rates were similar among all three ST groups suggesting that embryo development is not compromised (FIG. 8C). ESC lines were established from ST blastocysts and differentiated into neural progenitor cells (NPCs) cardiomyocytes, and teratomas. Comparable differentiation efficiencies were observed between mitochondrial respiratory chain (RC) enzyme activity and oxygen consumption rates (OCR) among ESC derivatives carrying 6 or 49 SNP differences (FIGS. 8D, 13A, 13B, 16A, and 16B). Interestingly, differentiated cells from an ST-ESC line with 33 SNP differences displayed significantly reduced OCR levels, alluding possible nuclear to mitochondrial incompatibility.

In summary, MRT in carrier oocytes by ST resulted in high fertilization and blastocyst development similar to controls. In addition, embryo development, ESC derivation and differentiation were not affected by donor mtDNA genetic background. However, it is possible that certain donor mtDNA may not function properly, a process that was independent of total SNP differences.

Example 11

Nuclear Genome Abnormalities

Because ST embryos may be at risk for chromosomal or sub-chromosomal abnormalities, expanded blastocysts derived from ST and control embryos were biopsied and examined by array CGH (comparative genome hybridization). A slightly higher aneuploidy rate was observed in both ST groups relative to intact controls but the difference was not significant. This could be related to older maternal age in the carrier group (FIGS. 14A and 17). Next, G-banding karyotype analysis was performed in ST and control ESCs. Abnormal karyotypes were observed in all groups but no significant differences were found. G-banding also detected cases of chromosomal mosaicism and polyploidy (FIGS. 14B and 18). Thus, to detect chromosomal abnormalities preimplantation genetic diagnosis can be performed prior to MRT embryo transfer.

Copy number variations (CNVs) were examined in selected ST-ES cell lines to explore possible subchromosomal abnormalities (deletion or duplications) (Lupski J R, Trends Genet 14, 417-422 (1998) and Sharp A J et al, Nat Genet 38, 1038-1042 (2006); both of which are incorporated by reference herein). De novo CNVs were detected in both ST and intact controls but were deemed of uncertain clinical significance (Kearny H M et al, Genet Med 13, 680-685 (2011); incorporated by reference herein).

In summary, a total of 6 ST blastocysts were produced from 4 ovarian stimulation cycles in carriers (Table 4). One blastocyst was aneuploid and four were eligible for transfer based on morphological quality assessments. These outcomes were comparable to controls.

TABLE 4

MRT outcomes for families with pathogenic mtDNA mutations

| | Family 1 | Family 2 | Family 3 | | | Family 4 | | Family 5 | | |
|---|---|---|---|---|---|---|---|---|---|---|
| Mitochondrial disease | LS | LS | LS | | | LS | | MELAS | | |
| Pathogenic mtDNA mutation | T8993G | T8993G | G13513A | | | No | | A3243G | | |
| Age of carrier (yr) | 22 | 23 | 36 | | | 28 | | 32 | | |
| COS | Yes | Yes | Yes | | | Excluded | | Yes | | |
| No. retrieved oocytes | 3 | 5 | 4 | | | n/a | | 11 | | |
| No. ST oocytes | 2 | Canceled | 4 | | | n/a | | 7 | | |
| ST blastocysts | 0 | n/a | 2 | | | n/a | | 4 | | |
| Grade at D6 | n/a | n/a | 5AA | 5BB | | n/a | | 5AA | 5BB | 5CC |
| Aneuploidy | n/a | n/a | Yes: +9 | n/t | | n/a | n/t | No | No | No |
| Sex | n/a | n/a | M | n/a | | n/a | n/a | M | F | F |
| mtDNA carryover | n/a | n/a | <1% | n/a | | n/a | n/a | <1% | <1% | <1%* |

Six ST embryos derived from oocytes carrying pathogenic mtDNA mutations reached the blastocyst stage. At least 2 blastocysts were eligible for transfer.
*mtDNA in ESCs from this blastocyst reverted to original maternal mtDNA haplotype but was wild type (did not carry A3243G mutation).
n/a, non-applicable;
n/t, non-tested.

Example 12

Maintenance of Donor mtDNA in ST Embryos and ESC Lines

MRT efficacy and safety depends not only on the degree of maternal mtDNA initially cotransferred with the karyoplast, but also on its subsequent persistence and possible amplification in embryos. Recent studies observed that due to genetic drift, some MRT ESCs restored maternal mtDNA (Yamada M et al, *Cell Stem Cell* 18, 749-754 (2016) and Hyslop L A et al, *Nature* 534, 383-386 (2016); both of which are incorporated by reference herein). Clearly, a small amount of maternal mtDNA carryover is common during ST resulting in low heteroplasmy in human embryos and in nonhuman primate offspring (typically below 2%) (Paull D et al, *Nature* 493, 632-637 (2013); incorporated by reference herein). Here, all examined ST zygotes and cleaving embryos (n=22) contained >99% donor mtDNA (Table 5) and similar outcomes were observed in 13 of 15 ES cell lines (87%) established from control ST blastocysts, regardless of donor mtDNA haplotype. However, 2 ESC lines from sibling ST embryos (ST-ES7 and ST-ES8), generated by combination of maternal U5a and donor H1b mtDNA (33 SNPs), displayed high levels of maternal mtDNA (81% and 94%) (Table 5). Extended passaging resulted in a complete loss of the donor mtDNA and return to the original maternal mtDNA haplotype (100%). Interestingly, two other genetically related ESC lines (ST-ES5 and ST-ES6) derived by reciprocal combination of maternal H1b and donor U5a showed high maintenance of donor mtDNA (>99%). Another ESC line generated from maternal U5a and donor V3 mtDNA (ST-ES9; 33 SNPs) also carried predominantly donor mtDNA.

TABLE 5

Donor mtDNA in human preimplantation MRT embryos and ESC lines

| | Carryover maternal mtDNA % | | | | | | | SNPs differences | | |
|---|---|---|---|---|---|---|---|---|---|---|
| | Preimplantation Embryos | | | ESCs | | | | | | |
| Treatment | Embryo stage | % | Lines | p.2-3 | p.9-10 | Maternal haplotype | Donor haplotype | Total | #Coding | D-loop |
| Control | n/t | | ST-ES1* | ≤1 | ≤1 | H56 | H2a | 6 | 4 | 1 |
| ST | n/t | | ST-ES2* | ≤1 | ≤1 | H2a | H56 | | | |
| | | | ST-ES3 | ≤1 | ≤1 | | | | | |
| | n/t | | ST-ES4* | ≤1 | ≤1 | H44a | H13a | 25 | 7 | 10 |
| | n/t | | ST-ES5 | ≤1 | ≤1 | H1b | U5a | 33 | 11 | 9 |
| | | | ST-ES6 | ≤1 | ≤1 | | | | | |
| | 4-cell | 0.7 | ST-ES7 | 81 ± 9 | 100 | U5a | H1b | | | |
| | 8-cell | 0.9 | | | | | | | | |
| | 10-cell | 0.4 | ST-ES8 | 94 ± 4 | 100 | | | | | |
| | 10-cell | 0.4 | | | | | | | | |
| | 1-cell | 0.4 | ST-ES9 | ≤1 | ≤1 | U5a | V3 | 33 | 11 | 9 |
| | 2-cell | 0.5 | | | | | | | | |
| | 8-cell | 0.5 | | | | | | | | |
| | Morula | 0.4 | ST-ES10 | ≤1 | ≤1 | V3 | U5a | | | |
| | 1-cell | 0.5* | ST-ES11* | ≤1 | ≤1 | H1e | D1f | 44 | 15 | 14 |
| | | 0.9* | ST-ES12* | ≤1 | ≤1 | | | | | |
| | n/a | 1.6* | | | | | | | | |
| | | 0.0* | ST-ES13* | ≤1 | ≤1 | | | | | |

TABLE 5-continued

Donor mtDNA in human preimplantation MRT embryos and ESC lines

| Treatment | Preimplantation Embryos Embryo stage | % | Lines | ESCs p.2-3 | p.9-10 | Maternal haplotype | Donor haplotype | SNPs differences Total | #Coding | D-loop |
|---|---|---|---|---|---|---|---|---|---|---|
| | 1-cell | 0.5 | ST-ES14 | ≤1 | ≤1 | D4a | A2g | 49 | 18 | 16 |
| | Morula | 0.2 | | | | | | | | |
| | Morula | 0.2 | | | | | | | | |
| | 1-cell | 0.2 | | | | | | | | |
| | 1-cell | 0.5 | ST-ES15 | ≤1 | ≤1 | A2g | D4a | | | |
| | 1-cell | 0.5 | | | | | | | | |
| | 1-cell | 0.5 | | | | | | | | |
| Carrier ST | 1-cell | 0.8 | n/a | | | H1b | H6a | 20 | 5 | 11 |
| | 3-cell | 0.5 | | | | | | | | |
| | 3-cell | 0.6 | | | | | | | | |
| | n/t | | 13513ST-ES | ≤1 | ≤1 | T2b | T2 | 22 | 3 | 5 |
| | 1-cell | 0.5 | 3243ST-ES1 | 20 ± 13 | 100 | H49 | B2k | 32 | 7 | 14 |
| | 8-cell | 0.8 | | | | | | | | |
| | 12-cell | 0.5 | 3243ST-ES2 | ≤1 | ≤1 | | | | | |
| | Morula | 0.5 | | | | | | | | |
| SCNT | n/t | | NT-ES1 | | ≤1 | H1b | H56 | 13 | 5 | 7 |
| | | | NT-ES2 | | ≤1 | | | | | |
| | | | NT-ES3 | | ≤1 | | | | | |
| | | | NT-ES4 | | ≤1 | | | | | |
| | | | NT-ES5 | | ≤1 | F1a | D1a | 47 | 16 | 11 |
| | | | NT-ES6 | | ≤1 | F1a | H1b | 38 | 13 | 13 |
| | | | NT-ES7 | ≤1 | ≤1 | X2c | U5a | 40 | 9 | 16 |
| | | | NT-ES8 | 19 ± 9 | 100 | X2c | D4a | 39 | 12 | 13 |

Among the three carrier ST-ESC lines, 3243ST-ES1 also contained a significant level of maternal mtDNA (20%) (Table 5). However, this maternal H49 haplotype did not include the A3243G mutation. Maternal mtDNA levels in this cell line gradually increased during extended culture to 90% at passage 8 and to homoplasmy at p.10 (FIG. 9A). Remarkably, another sibling ESC line (3243ST-ES2) generated by the same maternal and donor mtDNA combination did not show any increase in maternal mtDNA, presumably due to stochastic or bottleneck effects (Table 5).

The study was expanded to include eight ESC lines derived by SCNT (NT-ESCs) that also carry donor oocyte mtDNA (Table 5) (Tachibana M et al, Cell 153, 1228-1238 (2013); Ma H et al, Nature 524, 234-238 (2015); and Kang E et al, Cell Stem Cell 18, 625-636 (2016); incorporated by reference herein). MtDNA heteroplasmy dynamics were analyzed during extended passaging and identified that NT-ES8 displayed a gradual increase of maternal (somatic) mtDNA from 19% at p. 2 to 100% at p.10 (Table 5, FIG. 15A). Note that this NT-ESC line was generated by combination of maternal X2c and donor D4a mtDNA haplotypes (39 SNPs).

In conclusion, ST allows efficient replacement of oocyte mtDNA with very low carryover mtDNA in the resulting preimplantation embryos. The majority of ESCs derived from ST blastocysts maintained predominantly donor mtDNA. However, some ESC lines displayed gradual loss of the donor and reversion to the maternal mtDNA, requiring further research to better understand underlying mechanisms.

Example 13

Molecular and Cellular Mechanisms Contributing to Maintenance of Donor mtDNA

Based on the observation that specific haplotype combinations led to reversal to the maternal mtDNA, it was hypothesized that this could be due to preferential replication of specific mtDNA haplotypes or that certain mtDNA endow cells with growth advantages (Burgstaller J P et al, Mol Hum Reprod 21, 11-22 (2015) and Agaronyan K et al, Science 347, 548-551 (2015); both of which are incorporated by reference herein).

The highly polymorphic mtDNA D-loop region, called conserved sequence box II (CSBII) was focused on first. It has been previously shown that a rare polymorphism in the CSBII, namely G5AG7, affects efficiency of mitochondrial transcription termination and replication primer generation. When the donor and maternal mtDNA were compared in a total of 26 ESC lines with 18 different haplotype combinations it was observed that two "reversed" sibling ST-ES7 and ST-ES8 carried donor mtDNA with a G5AG8 polymorphism while the maternal mtDNA was G6AG8. Using in vitro transcription assays it was determined whether synthesis of the replication primer by mitochondrial RNA polymerase was affected in donor mtDNA. It was found that the deletion of a single guanosine residue (G5AG8 vs. G6AG8) in donor mtDNA results in a 4-fold reduction of replication primer synthesis (FIG. 9a). Therefore, certain mtDNA haplotypes varying in the CSBII sequence provide more efficient synthesis of the replication primer and, subsequently, may achieve replicative advantage. Without being bound by theory, this mechanism could explain the phenomenon of preferential replication of maternal mtDNA in some of the ESC lines. Sequence analysis did not find CSBII SNP differences in the remaining two reversed 3243ST-ES1 and NT-ES8. A number of other D-loop polymorphisms were observed including the core TAS region, which is also implicated in regulation of mtDNA replication (Jemt E et al, *Nucl Acids Res* 43, 9262-9275 (2015); incorporated by reference herein). Although the exact mechanism by which these polymorphisms affect replication remain unclear, it can be speculated that, similar to the CSBII and TAS regions, some D-loop variants may result in replication bias of a particular mtDNA haplotype.

It was also considered if additional replication-independent mechanisms affect the reversal to maternal mtDNA and examined the increase in maternal mtDNA in reversed 3243ST-ES1 and NT-ES8 in whole cultures or individual cell clones. Starting maternal mtDNA levels increased with passaging in whole cultures (FIGS. 9B, 9C, and 15A). However, when ESCs were disassociated into individual cells and cultured isolated single cell clones, the starting maternal mtDNA levels varied in different clones but the heteroplasmy did not change with extended culture (FIG. 9D). Significant differences in cell proliferation and growth rates among different clones were observed. Clones with higher maternal mtDNA levels exhibited significantly faster growth rates than clones with lower maternal mtDNA heteroplasmy (FIG. 9E). These results suggest that certain mtDNA haplotypes confer ESCs with faster growth and proliferative advantages. Thus, in mixed cultures consisting of cells with varying heteroplasmy, a sub-population of cells with higher maternal mtDNA may overgrow cells with donor mtDNA.

Mitochondrial respiratory chain complex I and complex IV enzyme activities were measured in cells carrying various mtDNA haplotypes but no significant differences were found. This suggests that the reversal to maternal mtDNA is independent of mitochondrial activity (FIG. 15B).

Next, it was examined if the reversal is specific to undifferentiated ESCs or could occur during differentiation. Several reversed and non-reversed ESCs were differentiated in vitro into NPCs and cardiomyocytes, and in vivo into teratomas. Maternal mtDNA levels were measured before and after differentiation (FIGS. 16A, 16B). Maternal mtDNA levels in the reversed 3243ST-ES1 reduced to undetectable levels in some tissues but were slightly elevated in other cell types compared to the initial 4% in undifferentiated ESCs (FIG. 9F). The maternal mtDNA was undetectable during in vivo and in vitro differentiation of the nonreversed sibling cell line 3243ST-ES2. In contrast, maternal mtDNA levels increased in all tested differentiated tissues in the reversed ST-ES7 and NT-ES8 (FIG. 9F). These results demonstrate that the mtDNA reversion phenomenon is not unique to ESCs and occurs during differentiation, raising the possibility that return to the mutant mtDNA may occur in some MRT children.

Example 14

Conclusions

The feasibility and clinical outcomes following MRT in oocytes carrying pathogenic mtDNA mutations was investigated 8, 10. Since mutations in either nuclear or mtDNA genes can cause similar mitochondrial syndromes, it is critical to conduct genetic testing to confirm the eligibility of women with pathogenic DNA mutations for MRT.

A range of heteroplasmy for mutant mtDNA was observed among different tested tissues in women carriers and their children. As expected, pathogenic mtDNA mutations were detected in oocytes from all carriers.

Carryover of the maternal mtDNA, while detectable, was below 1% in preimplantation ST embryos. However, reversion to the original maternal mtDNA was observed in a few MRT ESCs (15%, 4/26) during their extended culture or differentiation. Maternal mtDNA in ST monkeys was at expected low levels and did not increase with age in adults. However, a moderate increase in maternal mtDNA (16%) was seen in selected oocytes from ST females (Lee H S et al, *Cell Rep* 1, 506-515 (2012); incorporated by reference herein). This implies that despite efficient replacement of the mutant mtDNA in oocytes, some MRT children may still develop high mutation loads and mitochondrial disease.

Among the factors that might contribute to the mtDNA reversion, it appears that this phenomenon was irrespective of MRT methods (ST, PNT or SCNT), presence of pathogenic mtDNA mutations and the genetic distance measured in total SNPs between donor and maternal mtDNA. However, some specific haplotype combinations produced preferential increase of the maternal and gradual loss of the donor mtDNA. One of the possible mechanisms responsible for the observed reversal could be more efficient replication primer synthesis and thus bias towards preferential amplification of mtDNA haplotypes with specific CSBII sequence polymorphisms. The selection of compatible donor mtDNA harboring CSBII or other D-loop sequences similar to the maternal mtDNA would solve this problem. While the number of tested combinations in the disclosed study is small, the possible order of replication advantage in mtDNA haplotypes could be H56>H1b, U5a>H1b>F1a, U5a>X2c>D4a and H49>B2k. However, stochastic or bottleneck mtDNA amplification during early embryo development may also coexist.

Mitochondria not only generate energy but also regulate cell proliferation and apoptosis (Chan D C et al, *Cell* 125, 1241-1252 (2006); incorporated by reference herein). Disclosed herein are mtDNA haplotypes could affect cell growth and proliferation thus providing selective advantage for cells with maternal mtDNA. Future applications of MRT will require additional studies evaluating compatible donor mtDNA haplotypes to avoid OXPHOS dysfunction, differences in mtDNA replication, cell growth and recovery of mutant mtDNA (Koehler C M et al, *Genetics* 129, 247-255 (1991); incorporated by reference herein).

Example 15 mtDNA Sequencing

Specific mtDNA mutations and general haplotypes were determined in oocytes, blood, skin fibroblasts (SF) and/or urine by whole mtDNA sequencing using MiSeq or amplification refractory mutation system-quantitative polymerase chain reaction (ARMS-qPCR).

Example 16

Controlled Ovarian Stimulation (COS)

Baseline screening was conducted including a medical history and physical exam, assessment of body mass index (BMI), anti-mullerian hormone (AMH) level, and antral follicle count (AFC). Subjects underwent ovarian stimulation and oocyte retrieval employing standard IVF protocols and procedures.

Example 17

Spindle Transfer (ST)

ST was performed as follows: meiotic metaphase II (MII) spindles were visualized under polarized microscopy and isolated with minimal cytoplasm (karyoplast, host mtDNA). The karyoplast was then placed in the perivitelline space of an enucleated oocyte (cytoplast, donor mtDNA) and fused using HVJ-E (hemagglutinating virus of Japan-envelope).

Example 18

Oocyte Vitrification

Oocyte vitrification was performed as previously described using commercially available human oocyte vitrification & thawing kits (Vitrification kit and Vit. Warming kit, Life Global).

Example 19

Derivation of ES Cells and Culture

ST blastocysts were freed from their zonae pellucidae and plated on mEF feeder layers on 4-well culture dishes for 5-7 days at 37° C., 3% $CO_2$, 5% $O_2$, and 92% $N_2$ in medium (DMEM/F12 with 10% FBS, 10% KSR, 0.1 mM nonessential amino acids, 1 mM I-glutamine, 0.1 mM β-mercaptoethanol, 5 ng/ml basic fibroblast growth factor, 10 μM ROCK inhibitor). Attached blastocyst outgrowths were manually minced into small pieces, re-plated onto fresh plates and maintained in knockout DMEM medium (Invitrogen) supplemented with 20% KSR, 0.1 mM nonessential amino acids, 1 mM I-glutamine, 0.1 mM β-mercaptoethanol, penicillin-streptomycin and 4 ng/ml bFGF for further propagation and analysis. All cell lines were negative for mycoplasma contamination.

Example 20 mtDNA Transcription Assays

In vitro transcription anti-termination assays were performed using PCR-amplified templates containing region 202-481 of donor (H1b or host (U5a) mtDNA. The products of the transcription reactions were resolved by 20% PAGE containing 6 M urea and visualized by PhosphoImager (GE Health).

Example 21

Cell Growth and Proliferation Assays

ESCs were adapted to grow under feeder-free conditions on Matrigel matrix in mTeSRTM1 medium (STEMCELL technologies) (Wu J et al, *Nature* 521, 316-321 (2015); incorporated by reference herein). The cells were dissociated with Accutase (Life Technologies) for 2 min and approximately $10^5$ cells were seeded into each 60 mm dish. The cells were harvested were periodically harvested and counted using Countess Automated Cell Counter (Invitrogen).

Example 22

Neural Progenitor Cells (NPC) Differentiation and Culture

A previously published protocol with minor modifications was used for NPC differentiation. Briefly, ESCs were maintained on MEFs in CDF12 medium before NPC differentiation. CDF12 medium contained DMEM/F12 (Life Technology), 20% knockout serum replacement (Life Technologies), 2 mM Glutamax (Life Technologies), 0.1 mM NEAA (Life Technology), 0.1 mM β-mercaptoethanol (Life Technologies) and 4 ng/ml FGF2 (Peprotech). ESCs were disaggregated with Collagenase IV (Life Technologies) and allowed to grow to about 40% confluence. To initiate neural induction, cells were washed twice with DPBS 1× without calcium & magnesium (Corning Cellgro) and changed to Neural Induction Medium 1 (NIM-1: 50% Advanced DMEM/F12 (Invitrogen), 50% Neurobasal (Invitrogen), 1× B27 (Invitrogen), 1× N2 (Invitrogen), 2 mM GlutaMAX and 10 ng/ml hLIF (Peprotech), 4 uM CHIR99021 (Selleckchem), 3 uM SB431542 (Selleckchem), 2 uM Dorsomorphin (Sigma), and 0.1 uM Compound E (EMD Chemicals Inc.). After 2 days culture in in NIM-1 medium, cells were switched to Neural Induction Medium 2 (NIM-2: 50% Advanced DMEM/F12, 50% Neurobasal, 1× N2, 1× B27, 2 mM GlutaMAX and 10 ng/ml hLIF, 4 uM CHIR99021, 3 uM SB431542 and 0.1 uM Compound E). Cells were further cultured in NIM-2 for 5 days with daily medium change. At the last day in NIM-2 medium, cells were treated overnight with 10 uM Y27632 (Selleckchem) and 20-30 "dome"-shaped colonies were manually picked and digested with Accumax (Innovative Cell Technologies) for 10 minutes at 37° C. After Accumax treatment cells were gently disaggregated into single cells and re-plated onto Matrigel-coated 6-well plates at a density of about $3.5 \times 10^4$ per $cm^2$ in Neural Progenitor cell Maintenance Medium (NPMM: 50% Advanced DMEM/F12, 50% Neurobasal, 1× B27, 1× $N_2$, 2 mM GlutaMAX, 10 ng/ml hLIF, 3 uM CHIR99021 and 2 uM SB431542) supplemented with 10 uM Y27632. NPCs were maintained on Matrigel-coated dishes in NPMM. NPCs were passaged when reached around 70% to 80% confluence using Accumax and replated at a density of $3 \times 10^4$ per $cm^2$ with daily medium change. For the initial 6 passages, NPCs were pre-treated with 10 μM Y27632 overnight before and during cell splitting. The study was randomized, and the investigators were blinded to treatment allocations in collaborators' laboratories.

Example 23

Cardiomyocyte Differentiation

Cardiomyocyte differentiation was performed based on a GiWi (GSK3 inhibitor and Wnt inhibitor) protocol described previously (Lian X et al, Nat Protoc 7, 1235-1246 (2012); incorporated by reference herein). Briefly, ESCs were grown on Matrigel-coated plates in mTeSR1 medium to 80-90% confluence before passaging with Accutase and then re-seeded at 0.5-1.5 million cells per well in 12-well plates in 1 ml of mTeSR1 plus 10 μM Y27632. On day 5, cells were incubated with 6 to 12 μM CHIR99021 (Selleckchem) for 16-24 h and then medium replaced with 2 ml of RPMI/B27 (−insulin) and cultured for two days. On day 8, a 2 ml combined medium was prepared by mixing 1 ml medium collected from the 12-well plate and 1 ml fresh RPMI/B27 (−insulin) medium. Cells were then replaced with 2 ml combined medium with 5 μM IWP2 (Tocris) added and cultured for 48 h. At day 10, 2 ml of fresh RPMI/B27 (−insulin) was added to each well of the 12-well plate. Starting from day 12 medium was changed every three days with 2 ml/well of RMPI/B27 (+insulin). Contracting cardiomyocytes were observed as early as day 17 from the initial passaging of ESCs. Differentiated cell types were identified by immunocytochemistry as described previously.

Example 24

Teratoma Assay

ESCs were injected into the femoral region of 6-week-old, SCID male mice (Charles River). Mice with tumors were euthanized and teratomas were isolated, sectioned and histologically characterized for the presence of representative tissues as described previously.

Example 25

Assessment of Mitochondrial Function

Mitochondrial respiratory chain enzymatic activities (Complex I and IV) were measured by spectrophotometry, as described in, for example, Spinazzi M et al, *Nat Protoc* 7, 1235-1246 (2012); incorporated by reference herein. Briefly, intact mitochondria were isolated from fibroblasts and treated with and without 3 mM rotenone at a 340 nm wavelength for 5 min. Differences of absorbance per minute were obtained, and the specificity of COMI activity was estimated by the percentage of rotenone inhibition. For live cell oxygen consumption, a XF96 Extracellular Flux Analyzer (Seahorse Biosciences) was used to measure oxygen consumption rates (OCR) and extracellular acidification rates (ECAR) as described previously 29. Briefly, neural progenitor cells (NPCs) were seeded at a density of 30,000 cells per well of a XF96 cell culture microplate and incubated for 24 h to allow cells to attach. Prior to assay, NPCs were equilibrated for 1 h in unbuffered XF assay medium supplemented with 25 mM glucose, 1 mM sodium pyruvate, 2 mM glutamax, 1× nonessential amino acids and 1% (v/v) FBS in a non-CO2 incubator. Sequential compound injections of oligomycin (0.5 μg/ml), carbonyl cyanide 4-(trifluoromethoxy) phenylhydrazone (FCCP, 1 μM) and rotenone (0.5 μM)/antimycin A (1 μM) were used to measure the key parameters of mitochondrial respiration. Indices of mitochondrial function were calculated as basal respiration rate (baseline OCR—rotenone/antimycin A OCR), ATP dependent (basal respiration rate—oligomycin OCAR), maximal respiration rate (FCCP OCR—rotenone/antimycin A OCR) and oxidative reserve (maximal respiration rate—basal respiration rate). Each plotted value was the mean of a minimum of 4 replicate wells, and was normalized to total cell numbers plated. Results were presented as means±SEM. One-way ANOVA was used for three group comparisons and student's t test was used for pairwise comparisons. A P-value less than 0.05 was considered as significant. The study was randomized, and the investigators were blinded to sample allocations among different groups.

Example 26 mtDNA Sequencing by MiSeq

DNA was extracted from skin fibroblasts, whole blood, Urine, ESCs and teratoma tissues using Gentra DNA extraction kit (Qiagen), and from oocytes using Pico Pure DNA Extraction Kit (Life Technologies). mtDNA was amplified by a single PCR reaction. mtDNA amplification from individual oocytes was performed using 2 primer sets: 7272F 5-GGCTCATTCATTTCTCTAACAG-3, 15712R 5-TTGGCTTAGTGGGCGAAATA-3 and 15635F 5-TCCATCCTCATCCTAGCAAT-3, 7401R 5-GGGGGCATCCATATAGTCAC-3 and mitochondrial sequencing performed.

Example 27

Detection of mtDNA Variants by Sanger Sequencing mtDNA variants present at over 10% heteroplasmy were corroborated independently by Sanger sequencing. Regions of mtDNA containing germline mutations or SNPs were amplified by PCR with previously reported primer sets using PCR Platinum SuperMix high fidelity kit (Life Technologies. PCR products were purified, sequenced and analyzed by Sequencher v. 5.0 (GeneCodes).

Example 28

ARMS-qPCR and Copy Number Measurement

The amplification refractory mutation system quantitative PCR assay (ARMs-qPCR) was performed to verify heteroplasmy at mt8993T>G, mt13513G>A and mt3243A>G and to measure carryover in control ST embryos and ES cells at 7843A>G, 16519T>C and 16278T>C8. Measurement of mtDNA copy number was performed.

Example 29

Genetic and Cytogenetic Analyses

Karyotyping by G-banding was performed on 20 metaphase cells from each human cell line. Array CGH was performed by IVI Gen. CNVs were identified by SNP genotyping as previously described in Ma H et al, *Nature* 511, 177-183 (2014) incorporated by reference herein and analyzed by a clinical genetic diagnosis laboratory.

Example 30

Statistical Analysis

Results are presented as means±SD. or SEM. p<0.05 was considered significant. Data were analyzed using Pearson non-parametric test for correlation, independent group t-test or chi-square test for pairwise comparison and ANOVA with Bonferroni analysis for multiple comparisons (IBM SPSS).

The invention claimed is:
1. A method for preparing a viable human oocyte for fertilization, the method comprising the steps of:
   a) isolating a first oocyte containing a polar body;
   b) gaining access through the zona pellucida of the first oocyte;
   c) removing the polar body from the first oocyte in a first medium comprising cytochalasin B and at least 10% human tubal fluid, using a Polarized Microscope Imaging System and laser drilling;
   d) removing the nuclear spindle from a second oocyte in a second medium comprising cytochalasin B and at least 10% human tubal fluid, using a Polarized Microscope Imaging System and laser drilling to create an enucleated cytoplast;

e) fusing the polar body removed from the first oocyte into the perivitelline space of the enucleated cytoplast in a third medium comprising hemagglutinating virus of Japan envelope (HVJ-E), thereby producing the viable human oocyte.

2. The method of claim 1 further comprising fertilizing the viable human oocyte via in vitro fertilization, thereby creating an embryo.

3. The method of claim 2 further comprising implanting the embryo in a receptive uterus.

4. The method of claim 1 wherein the second medium further comprises HEPES buffer.

5. The method of claim 1 wherein the first medium further comprises HEPES buffer.

6. The method of claim 2, further comprising culturing the embryo to the blastocyst stage prior to implanting the embryo in the receptive uterus.

* * * * *